US008166909B2

(12) United States Patent
Chappa

(10) Patent No.: US 8,166,909 B2
(45) Date of Patent: May 1, 2012

(54) APPARATUS AND METHODS FOR APPLYING COATINGS

(75) Inventor: Ralph A. Chappa, Prior Lake, MN (US)

(73) Assignee: Surmodics, Inc., Eden Prairie, MN (US)

( * ) Notice: Subject to any disclaimer, the term of this patent is extended or adjusted under 35 U.S.C. 154(b) by 438 days.

(21) Appl. No.: 11/559,817

(22) Filed: Nov. 14, 2006

(65) Prior Publication Data

US 2007/0128343 A1 Jun. 7, 2007

Related U.S. Application Data

(60) Provisional application No. 60/736,995, filed on Nov. 15, 2005.

(51) Int. Cl.
*B05B 7/06* (2006.01)
(52) U.S. Cl. ............ 118/313; 239/9; 239/543; 239/102; 118/500; 118/200; 118/232; 118/20; 118/642; 525/242; 427/2.1
(58) Field of Classification Search .................... 427/2.1, 427/430.1, 429; 239/102, 9, 543; 525/242; 118/500
See application file for complete search history.

(56) References Cited

U.S. PATENT DOCUMENTS

| | | | |
|---|---|---|---|
| 2,335,116 A | 11/1943 | Hansen | |
| 3,966,120 A * | 6/1976 | Furgalus et al. | ............ 239/102.2 |
| 4,352,459 A | 10/1982 | Berger et al. | |
| 4,824,017 A * | 4/1989 | Mansfield | .......................... 239/9 |
| 5,219,120 A | 6/1993 | Ehrenberg et al. | |

(Continued)

FOREIGN PATENT DOCUMENTS
DE 10053826 5/2002
(Continued)

OTHER PUBLICATIONS

"International Search Report (ISR) from PCT", International Search Report and Written Opinion,12 pages.

(Continued)

*Primary Examiner* — Dah-Wei Yuan
*Assistant Examiner* — Andrew Bowman
(74) *Attorney, Agent, or Firm* — Pauly, Devries Smith & Deffner, L.L.C.

(57) ABSTRACT

The invention relates to systems and methods for forming coatings that can elute active agents and coating produced by the same. In an embodiment, the invention includes an apparatus for applying a coating to a medical device including a first spray nozzle, a first coating composition supply conduit, a second spray nozzle, and a second coating composition supply conduit. In an embodiment, the invention includes a method of applying a coating to a medical device including forming a first spray stream, forming a second spray stream, and directing the spray streams toward the medical device so that the first spray stream intersects the second spray stream before hitting the medical device. In an embodiment, the invention includes an apparatus for applying a coating to a medical device including a spray nozzle, a first coating composition supply conduit and a second coating composition supply conduit. In an embodiment, the invention includes a method of applying a coating to a medical device including applying a first composition onto the surface of a spray nozzle, applying a second composition onto the surface of the spray nozzle, generating a spray stream comprising the first composition and the second composition with the nozzle and directing the spray stream at the medical device.

16 Claims, 12 Drawing Sheets

U.S. PATENT DOCUMENTS

| | | | |
|---|---|---|---|
| 5,466,233 | A | 11/1995 | Weiner et al. |
| 5,679,400 | A | 10/1997 | Tuch |
| 6,218,016 | B1 | 4/2001 | Tedeschi et al. |
| 6,303,148 | B1 | 10/2001 | Hennink et al. |
| 6,695,920 | B1 * | 2/2004 | Pacetti et al. ............... 118/500 |
| 6,709,712 | B2 | 3/2004 | Chappa et al. |
| 6,719,750 | B2 | 4/2004 | Varner et al. |
| 7,077,910 | B2 | 7/2006 | Chappa et al. |
| 7,125,577 | B2 | 10/2006 | Chappa |
| 7,192,484 | B2 | 3/2007 | Chappa et al. |
| 2002/0107330 | A1 * | 8/2002 | Pinchuk et al. ............... 525/242 |
| 2003/0014036 | A1 | 1/2003 | Varner et al. |
| 2004/0133155 | A1 | 7/2004 | Varner et al. |
| 2005/0019371 | A1 | 1/2005 | Anderson et al. |
| 2005/0059956 | A1 | 3/2005 | Varner et al. |
| 2005/0143363 | A1 | 6/2005 | De Juan et al. |
| 2005/0196518 | A1 * | 9/2005 | Stenzel ............... 427/2.1 |
| 2005/0255142 | A1 | 11/2005 | Chudzik et al. |
| 2005/0271703 | A1 | 12/2005 | Anderson et al. |
| 2005/0271706 | A1 | 12/2005 | Anderson et al. |
| 2005/0276837 | A1 | 12/2005 | Anderson et al. |
| 2005/0281863 | A1 | 12/2005 | Anderson et al. |
| 2005/0287188 | A1 | 12/2005 | Anderson et al. |
| 2006/0088653 | A1 | 4/2006 | Chappa |
| 2006/0110428 | A1 | 5/2006 | De Juan et al. |
| 2006/0165872 | A1 | 7/2006 | Chappa et al. |
| 2007/0065481 | A1 | 3/2007 | Chudzik et al. |

FOREIGN PATENT DOCUMENTS

| | | |
|---|---|---|
| EP | 0096433 | 12/1983 |
| FR | 2733163 | 10/1996 |
| GB | 2301296 | 12/1996 |

OTHER PUBLICATIONS

"Ultrasonic Spray Nozzle Systems", *SONO-TEK Corporation Brochure*, (2005), 16 pages.

Yeo, Yoon, "A New Microencapsulation Method Using an Ultrasonic Atomizer Based on Interfacial Solvent Exchange", *Journal of Controlled Release 100*, (2004), pp. 379-388.

* cited by examiner

APPARATUS AND METHODS FOR APPLYING COATINGS

This application claims the benefit of U.S. Provisional Application No. 60/736,995, filed Nov. 15, 2005, the contents of which are herein incorporated by reference.

FIELD OF THE INVENTION

The invention relates to apparatus and methods for applying coatings to devices. More specifically, the invention relates to apparatus and methods for applying coatings that can elute active agents and coatings produced by the same.

BACKGROUND OF THE INVENTION

Therapeutic benefits can be realized by administering an active agent to a subject over an extended period of time. To this end, controlled-release drug delivery systems have been developed to control the rate of drug delivery to the subject. Controlled-release drug delivery systems can include both delayed release and sustained release systems.

Site-specific drug delivery can also offer therapeutic benefits. Site-specific drug delivery refers to the delivery of an active agent to a specific target tissue site, instead of systemically. Site-specific drug delivery offers advantages because the effect of the active agent on the target tissue can be enhanced while side effects of the active agent on other tissues can be reduced.

One technique for providing controlled-release site-specific drug delivery is to use a drug-eluting coating system disposed on a medical device. The coating can serve to control the rate at which the active agent is eluted while the fact that the coating is disposed on a medical device allows delivery of the active agent to be site-specific. As an example of this approach in use, stents with drug-eluting coatings are routinely inserted into patients to prevent restenosis of the stented artery.

The application of active-agent eluting coatings to medical devices remains technically challenging. Therefore, a need exists for coating apparatus and methods that can be used to apply coatings to devices and coatings produced by the same.

SUMMARY

The invention relates to apparatus and methods for applying coatings that can elute active agents and coatings produced by the same. In an embodiment, the invention includes an apparatus for applying a coating to a medical device including a first spray nozzle, a first coating composition supply conduit configured to deliver a first coating composition to the first spray nozzle, a second spray nozzle, a second coating composition supply conduit configured to deliver a second coating composition to the second spray nozzle, the first and second spray nozzles arranged to produce first and second spray streams that intersect one another, and a device holder configured to hold a medical device in the path of the first and second spray streams.

In an embodiment, the invention includes a method of applying a coating to a medical device including forming a first spray stream by applying a first coating composition onto a first spray nozzle, forming a second spray stream by applying a second coating composition onto a second spray nozzle, and directing the spray streams toward the medical device so that the first spray stream intersects the second spray stream before hitting the medical device.

In an embodiment, the invention includes an apparatus for applying a coating to a medical device including a spray nozzle, a first coating composition supply conduit configured to deliver a first coating composition onto the exterior surface of the spray nozzle, and a second coating composition supply conduit configured to deliver a second coating composition onto the exterior surface of the spray nozzle.

In an embodiment, the invention includes a method of applying a coating to a medical device including applying a first composition onto the surface of a spray nozzle, applying a second composition onto the surface of the spray nozzle, generating a spray stream comprising the first composition and the second composition with the nozzle, and directing the spray stream at the medical device.

In an embodiment, the invention includes a combination including a medical device including a substrate surface, and a coating disposed on the substrate surface, the coating including the coating composition including an active agent and a first solvent, and a polymer and a second solvent, the second solvent including a component immiscible with the first solvent, the coating composition configured to release an active agent over time when implanted in vivo.

In an embodiment, the invention includes a coating layer configured to control elution of an active agent including a first polymer and a second polymer, the coating defining an inner surface and an outer surface. The concentration of the first polymer is relative to the second polymer forming a concentration gradient between the inner surface and the outer surface.

In an embodiment, the invention includes an active agent eluting coating layer including a first polymer, a second polymer, and an active agent, the coating defining an inner surface and an outer surface, wherein the concentration of the first polymer relative to the second polymer increases continuously between the inner surface and the outer surface.

The above summary of the present invention is not intended to describe each discussed embodiment of the present invention. This is the purpose of the figures and the detailed description that follows.

BRIEF DESCRIPTION OF THE DRAWINGS

The invention may be more completely understood in connection with the following drawings, in which.

Figure 1:
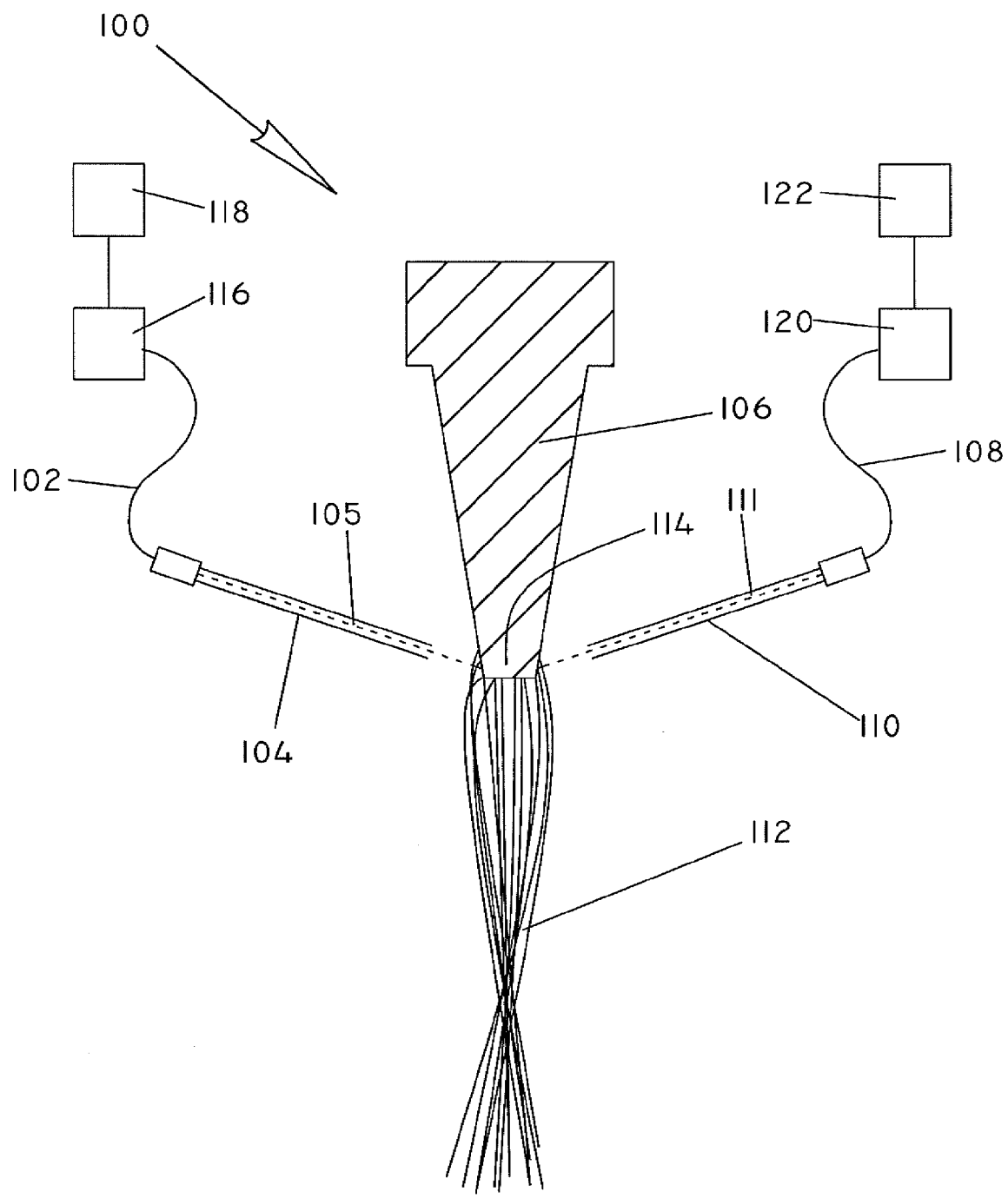
FIG. 1 is a schematic side view of a coating apparatus in accordance with an embodiment of the invention.

While the invention is susceptible to various modifications and alternative forms, specifics thereof have been shown by way of example and drawings and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The use of drug-eluting coating systems disposed on medical devices can offer therapeutic advantages. Specifically, controlled-release site-specific drug delivery can be achieved, maximizing active agent concentration at the target tissue site while limiting potentially undesirable side effects on non-targeted tissue. This approach has proven successful in the context of many medical devices such as coated drug-eluting stents, as the restenosis rate for coated stents has been shown to be dramatically lower than comparable bare metal stents.

Many drug-eluting coating systems contain one or more polymeric components. Frequently, solvents are used to keep the polymer(s) in solution before application of the coating system to the medical device. A range of different solvents can be used depending on the solubility requirements of the particular polymers used. Where active agent(s) are part of the same coating layer as the polymer(s), the active agents are frequently mixed into the same solution as the polymer.

However, in some cases it can be desirable to keep the active agent separate from the polymer, such as where the polymer and the active agent require incompatible solvents. An example of this can be illustrated with respect to coating systems including relatively hydrophobic polymers and relatively hydrophilic macromolecular active agents. Macromolecular active agents are one type of active agent that can be used to treat various conditions. Macromolecular activate agents can be defined as those active agents having a molecular weight (or average molecular weight) of greater than about 10 kD (1 kilodalton is equal to 1,000 atomic mass units). By way of example, macromolecular active agents can include antibodies, antibody derivatives, cytokines, fusion proteins, polynucleotides, and the like. Many macromolecular agents, such as antibodies and other sorts of proteins, are primarily soluble in aqueous, or water based, solvent systems. When using such macromolecular active agents in a coating system with polymers that are primarily soluble in non-polar organic solvents, challenges can be encountered. Specifically, combining the two can result in a viscous heterogeneous mixture that is unsuitable for spray application on to a medical device. In other instances, combining the two can result in significant phase separation before and/or after application of the coating on to the surface of the medical device.

One approach to overcoming incompatibility issues is to form emulsions of the incompatible components prior to applying the coating onto the substrate. However, emulsions can suffer from poor stability, can have viscosities high enough to hinder spray application, and can adversely affect stability of some active agents such as proteins.

Embodiments of the present invention can be used to apply coatings with incompatible components. Specifically, embodiments of the present invention can be used to form coatings by separately delivering a first component and a second component to the substrate of a medical device in a manner that limits or controls mixing of the components prior to application.

Embodiments of the present invention can also be used to apply coatings with compatible components. In some instances, it can be desirable to deliver components to a substrate surface separately even when the components are compatible. For example, if a multi-layer coating is to be formed with a base layer containing polymer and an active agent and a top layer containing only polymer, this can be more easily accomplished if the polymer and the active agent are delivered a spray nozzle separately, or are delivered to separate spray nozzles. Specifically, when applying the base layer, both the polymer composition and the active agent composition can be delivered to a spray nozzle, or spray nozzles, and when applying the top layer the active agent composition delivery can simply be shut off. Embodiments of the present invention can also be used to form coatings having concentration gradients. For example, the application rate of one polymer can be varied with respect to another during the coating process so that there is a concentration gradient through the thickness of the coating layer.

The term "coating composition", as used herein, shall refer to a composition such as a solution that is later atomized and sprayed to form a coating, or a part of a coating, and includes one or more polymers, one or more active agents, or both one or more polymers and one or more active agents. Coating compositions can also include other components such as solvents, stabilizers, salts, and the like.

The term "polymer composition", as used herein, shall refer to a coating composition that includes one or more polymers but not active agents. The term "active agent composition", as used herein, shall refer to a coating composition that includes one or more active agents but not polymers. Both polymer compositions and active agent compositions can include other components such as solvents, stabilizers, salts, and the like.

Some embodiments of the invention will now be described with reference to the figures. FIG. 1 shows a schematic side view of a coating apparatus 100 in accordance with an embodiment of the invention. A first composition supply line 102 connects to a first composition delivery conduit 104 that applies a first coating composition 105 onto the exterior surface of a nozzle 106. The first composition delivery conduit 104 can be separated from the nozzle 106 by an air gap. The first composition delivery conduit 104 can be made from various materials including hypodermic needle tube stock, plastic tubing, etc. The nozzle 106 has an atomization surface 114. The nozzle 106 can be an ultrasonic-atomization type spray nozzle (or ultrasonic nozzle).

Ultrasonic nozzles transmit vibrational energy to a liquid in an amount sufficient to atomize the liquid and form a spray of droplets. Ultrasonic nozzles are available commercially, such as from Sono-Tek, Milton, N.Y. Different types and sizes of ultrasonic nozzles may be used depending on the specific coating compositions used and the desired attributes of the spray stream generated. Ultrasonic nozzles may be designed to operate at specific frequencies. In an embodiment, a 60 KHz ultrasonic nozzle can be used. The desired power level for operating the ultrasonic nozzle may depend on various factors including the size and design of the nozzle, the viscosity of the composition being used, the volatility of components in the composition being used, etc. In some embodiments, the ultrasonic nozzle is operated at a power range of about 0.3 watts to about 3.0 watts. In an embodiment, the ultrasonic nozzle is operated at a power range of about 0.5 watts to about 1.5 watts. Exemplary ultrasonic nozzles are described in U.S. Pat. No. 4,978,067, the contents of which is herein incorporated by reference.

The first composition supply line 102 is connected to a first pump 116 and a first composition supply reservoir 118. The first pump 116 can be set to deliver the first coating composition 105 at any desired rate. By way of example, the first pump 116 can be set to deliver the first coating composition 105 at a rate of from about 0.001 ml/minute to about 20 ml/minute. In an embodiment, the first pump 116 delivers the first coating composition 105 at a rate of about 0.01 ml/minute to about 1.0 ml/minute. The rate at which the first pump 116 delivers the first coating composition 105 can be varied during the coating process. The first pump 116 can be controlled by an electronic controller unit (not shown) such as a programmable logic controller (PLC) and/or a computer. The first coating composition 105 is converted into a spray stream 112 by the nozzle 106. In an embodiment, the first coating composition 105 is atomized by the nozzle 106.

A second composition supply line 108 connects to a second composition delivery conduit 110 which applies the second coating composition 111 onto the exterior surface of nozzle 106. The second composition delivery conduit 110 can be made from various materials including hypodermic needle tube stock, plastic tubing, etc. The second composition supply line 108 is connected to a second pump 120 and a second composition supply reservoir 122. The second pump 120 can be set to deliver the second coating composition 111 at any desired rate. By way of example, the second pump 120 can be set to deliver the second coating composition 111 at a rate of from about 0.001 ml/minute to about 20 ml/minute. In an embodiment, the second pump 120 delivers the second coating composition 111 at a rate of about 0.01 ml/minute to about 1.0 ml/minute. The rate at which the second pump 120 delivers the second coating composition 111 can be varied during the coating process independently of the rate of the first pump 116. The second pump 120 can be controlled by a controller unit (not shown). The second coating composition 111 is converted into a spray stream 112 by the nozzle 106. In an embodiment, the second coating composition 111 is atomized by the nozzle 106.

The pumping rate of the first pump 116 and the pumping rate of the second pump 120 can be the same or different. As an example, the pumping rates of the pumps can be manipulated so that more of one coating composition (105 or 111) is applied than the other. The pumping rate of the first pump 116 and the pumping rate of the second pump 120 may be constant or variable over time.

The first coating composition 105 and the second coating composition 111 may be applied to the nozzle 106 either simultaneously or sequentially. In an embodiment, first coating composition 105 and second coating composition 111 are applied to the nozzle 106 simultaneously. In some embodiments, the first coating composition 105 and the second coating composition 111 do not contact each other until after they are applied to the surface of the nozzle 106. While not intending to be bound by theory, it is believed that because both compositions are rapidly atomized after being applied onto the nozzle 106 that they do not phase separate significantly, even where the solvents are incompatible. Therefore, embodiments of the invention can reduce problems associated with using incompatible solvents.

The first coating composition 105 and/or the second coating composition 111 can include a polymer. In some embodiments, the first coating composition 105 and/or the second coating composition 111 contains an active agent. The first coating composition 105 and/or the second coating composition 111 can also include one or more solvents. Many different solvents can be included depending on the polymer(s) and active agent(s) being used. In some embodiments, solvents of the first coating composition 105 and the second coating composition 111 are immiscible with each other. In other embodiments, solvents of the first coating composition 105 and the second coating composition 111 are miscible with each other.

While not shown, it will be appreciated that the coating apparatus may also include other components used with spraying equipment including such components as an air supply source that functions to guide the spray stream 112 downward forming a concentration point for precise coating of a substrate.

In some embodiments, conditions such as temperature, pressure and humidity can be controlled in the area of the spray stream and substrate. For example, humidity can be controlled in any suitable manner, including at the time of preparing and/or using (as by applying) the composition, for instance, by coating the surface in a confined chamber or area adapted to provide a relative humidity different than ambient conditions.

Figure 2:
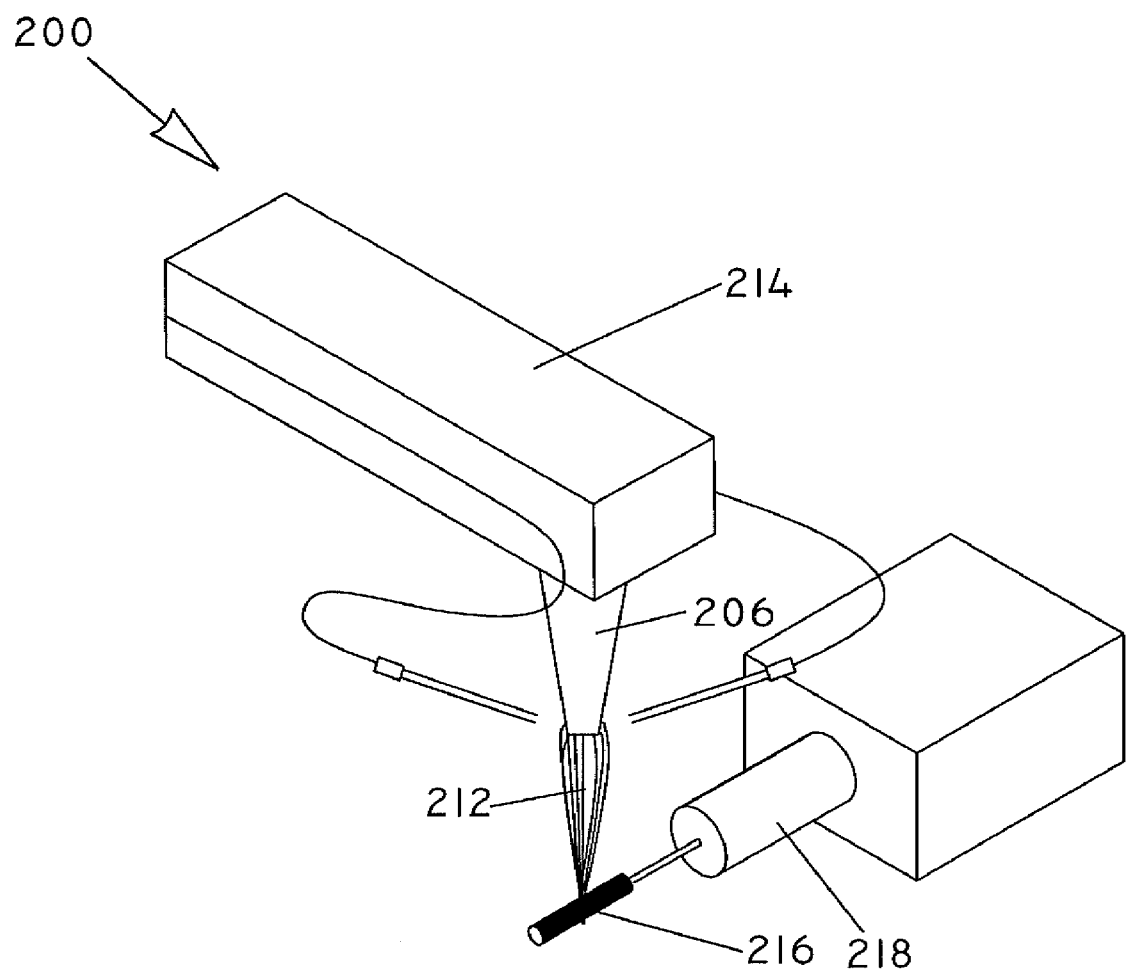
FIG. 2 is a schematic perspective view of a coating apparatus in accordance with an embodiment of the invention.

FIG. 2 shows a schematic perspective view of a coating apparatus 200 (not to scale) in accordance with an embodiment of the invention. In this view, a spray stream 212 generated by a nozzle 206 is applied to a medical device 216. The medical device 216 can be attached to a rotator device 218 in order to expose different sides of the medical device 216 to the spray stream 212. The rotator device 218 can include a pin vise. The rotator device 218 can include an electric motor and an electronic controller to control rotation of the medical device. In some embodiments, the rotator device can include a pair of rollers that can turn in order to rotate the device. The coating apparatus 200 can also include components as described in U.S. Pub. App. Nos. 2003/0190420, 2004/0062875, 2004/0194704, 2005/0158449, 2006/0088653 and 2006/0165872, the contents of which are all herein incorporated by reference. The nozzle 206 can be connected to a sprayer arm 214 that can move the nozzle 206 as desired, such as back and forth, laterally, etc. The sprayer arm 214 can be connected to a rail support (not shown) to facilitate movement of the sprayer arm 214 as desired.

Figure 3:
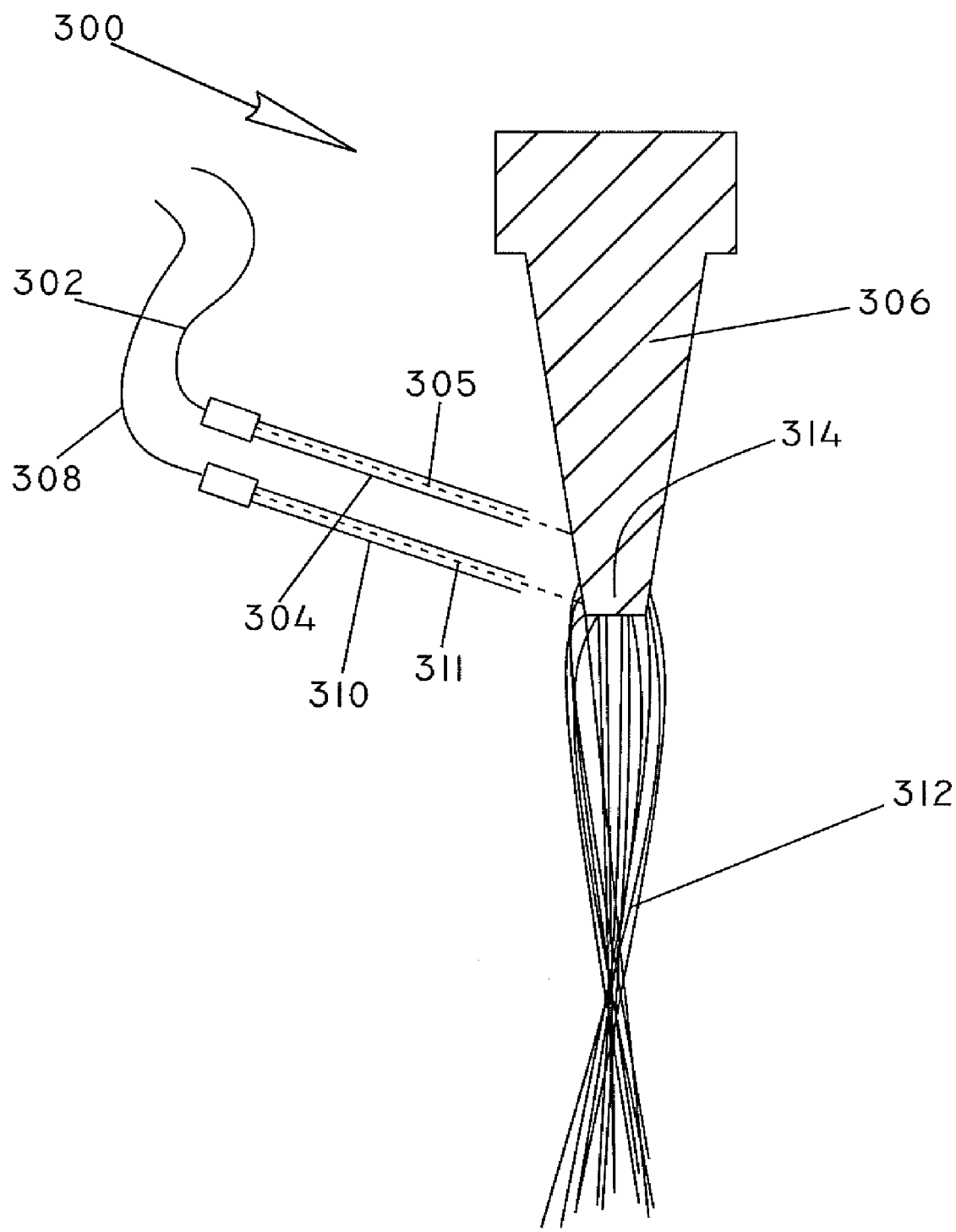
FIG. 3 is a schematic side view of a coating apparatus in accordance with another embodiment of the invention.

FIG. 3 shows a schematic side view of a coating apparatus 300 in accordance with another embodiment of the invention. A first composition supply line 302 connects to a first composition delivery conduit 304 that applies a first coating composition 305 onto the nozzle 306. The nozzle 306 has an atomization surface 314. In an embodiment, the nozzle 306 is an ultrasonic nozzle. The first composition supply line 302 is connected to a pump (not shown) and a first composition supply reservoir (not shown). The first coating composition 305 is converted into a spray stream 312 by the nozzle 306. A second composition supply line 308 connects to a second composition delivery conduit 310 that applies a second coating composition 311 onto the nozzle 306. The second composition supply line 308 is connected to a pump (not shown) and a second composition supply reservoir (not shown). The second coating composition 311 is converted into a spray stream 312 by the nozzle 306. In this embodiment, the first composition delivery conduit 304 is positioned vertically above the second composition delivery conduit 310. While not intending to be bound by theory, it is believed that this configuration can affect the atomization process because the first composition must run down the nozzle 306 and briefly contact the second composition before both are atomized at the atomization surface.

Figure 4:
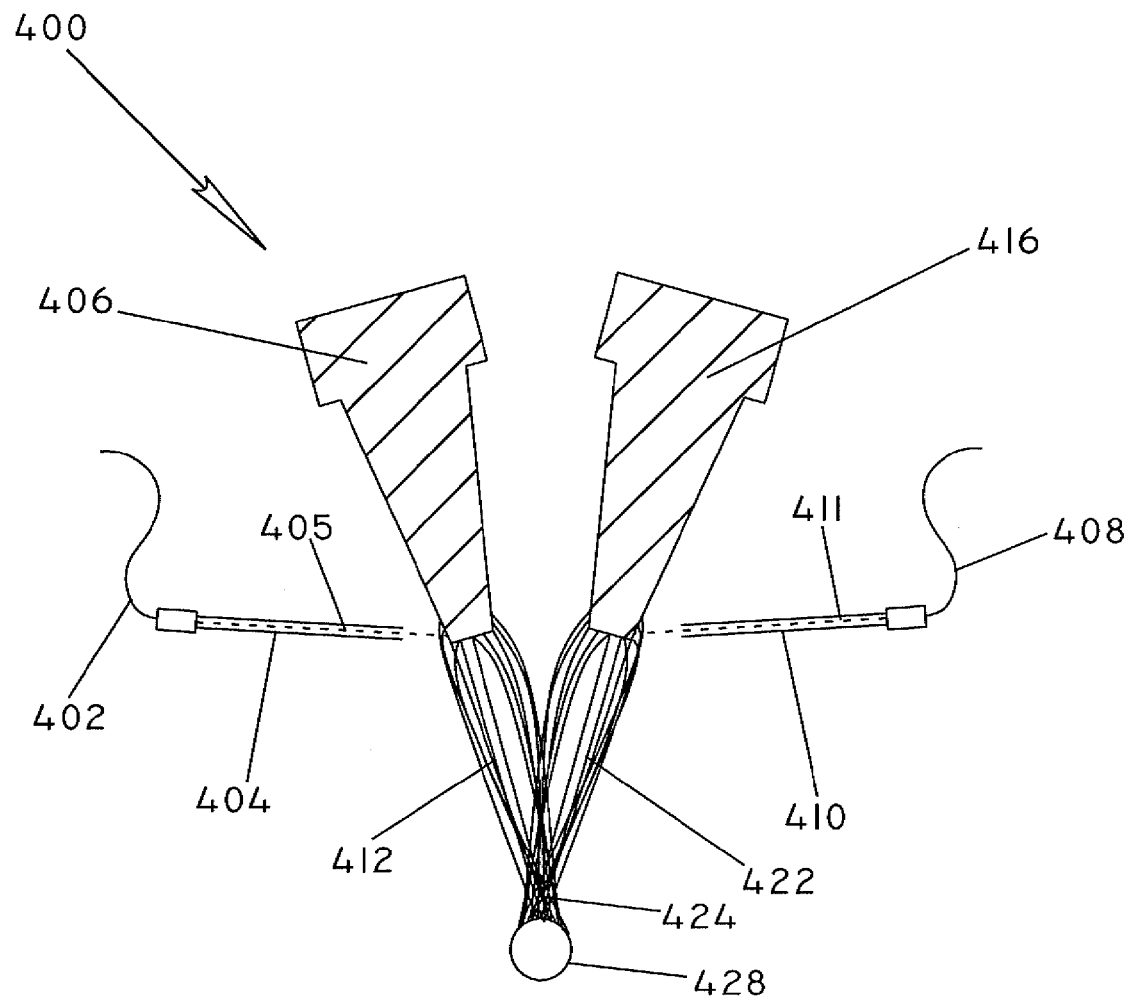
FIG. 4 is a schematic side view of a coating apparatus in accordance with another embodiment of the invention.

In some embodiments, the spraying apparatus can include two spray nozzles. Referring to FIG. 4, a schematic side view of a coating apparatus 400 in accordance with another embodiment of the invention is shown. In this embodiment, there is a first nozzle 406 and a second nozzle 416. A first composition supply line 402 connects to a first composition delivery conduit 404 that applies the first coating composition 405 onto the first nozzle 406. The first composition supply line 402 is connected to a pump (not shown) and a first composition supply reservoir (not shown). The pump can be set to deliver the first coating composition 405 at any desired rate. The first coating composition 405 is converted into a spray stream 412 by the nozzle 406.

A second composition supply line 408 connects to a second composition delivery conduit 410 that applies the second coating composition 411 onto the second nozzle 416. The second composition supply line 408 is connected to a pump (not shown) and a second composition supply reservoir (not shown). The pump can be set to deliver the second composition at any desired rate. The second coating composition 411 is converted into a spray stream 422 by the second nozzle 416. In this embodiment, the first coating composition 405 and the second coating composition 411 do not contact each other until their respective spray streams 412 and 422 meet at a point of intersection 424. After the spray streams 412 and 422 intersect, they proceed to contact the medical device 428 to be coated. In this embodiment, the point of intersection 424 is between the spray nozzles 406 and 416 and the medical device 428. In other embodiments, the point of intersection 424 is not between the spray nozzles 406 and 416 and the medical device 428.

While not intending to be bound by theory, it is believed that in some embodiments it can be desirable to aim the spray streams such that they intersect before the spray streams encounter the medical device. For example, when spraying different coating compositions with immiscible solvents from different spray nozzles, it has been observed that the compositions can exhibit a reduced degree of phase separation on the surface of the medical device when the spray streams intersect before contacting the surface of the medical device.

Figure 5:
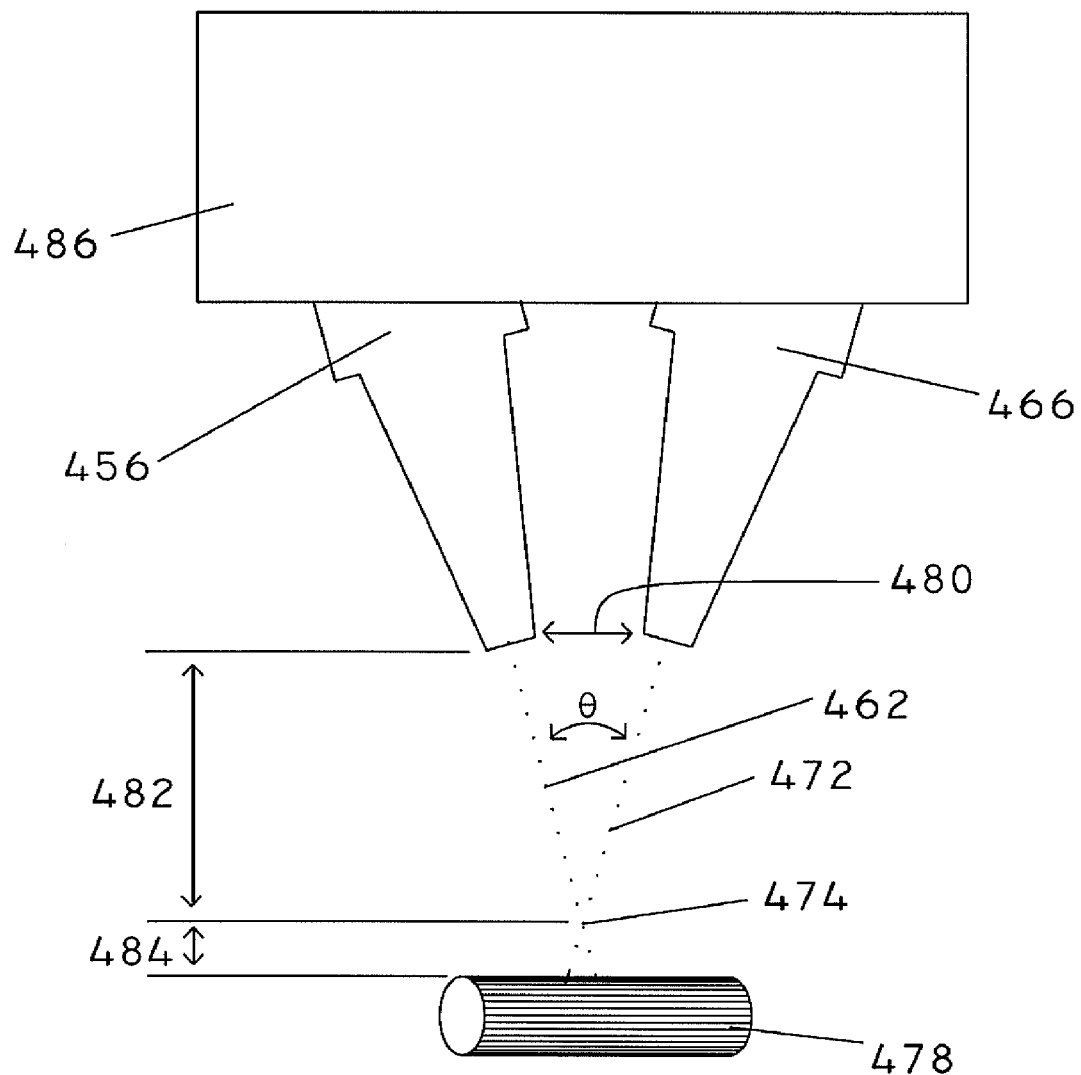
FIG. 5 is a schematic side view of a coating apparatus in accordance with an embodiment of the invention.

Referring now to FIG. 5, a schematic side view of two spray nozzles 456, 466 attached to a spray arm 486 is shown. In this view, dotted line 462 represents the center of a spray stream generated by spray nozzle 456, while dotted line 472 represents the center of a spray stream generated by spray nozzle 466. A substrate 478 is shown positioned below the spray nozzles 456, 466. The spray streams intersect each other at point 474 at angle θ. If angle θ is too small, the spray streams may not intersect within a reasonable distance from the spray tips. If angle θ is too large, a significant amount of the material being sprayed may not be deposited on the substrate 478 and end up as overspray. In some embodiments, angle θ can be from about 5 degrees to about 120 degrees.

If the distance between the nozzle tips is too large, the spray streams may travel farther before intersecting, becoming dispersed and less focused. This can result in an undesirable amount of overspray being generated. In some embodiments, the distance 480 between the tip of spray nozzle 456 and spray nozzle 466 is between about 0.1 cm and about 10 cm.

If the distance between the nozzle tips and the point of intersection is too large, the spray streams may be undesirably dispersed and unfocused before they intersect. Again, this can result in an undesirable amount of overspray being generated. In an embodiment, the distance 482 from the tips of spray nozzles 456 and 466 to point 474 can be from about 0.1 cm to about 10 cm.

If the distance between the point of intersection and the substrate to be coated, such as a medical device, is too large, the spray streams may become undesirably dispersed and more overspray will be created. In an embodiment, the distance 484 from point 474 to the substrate 478 is from about 0.1 cm to about 5 cm.

Figure 6:
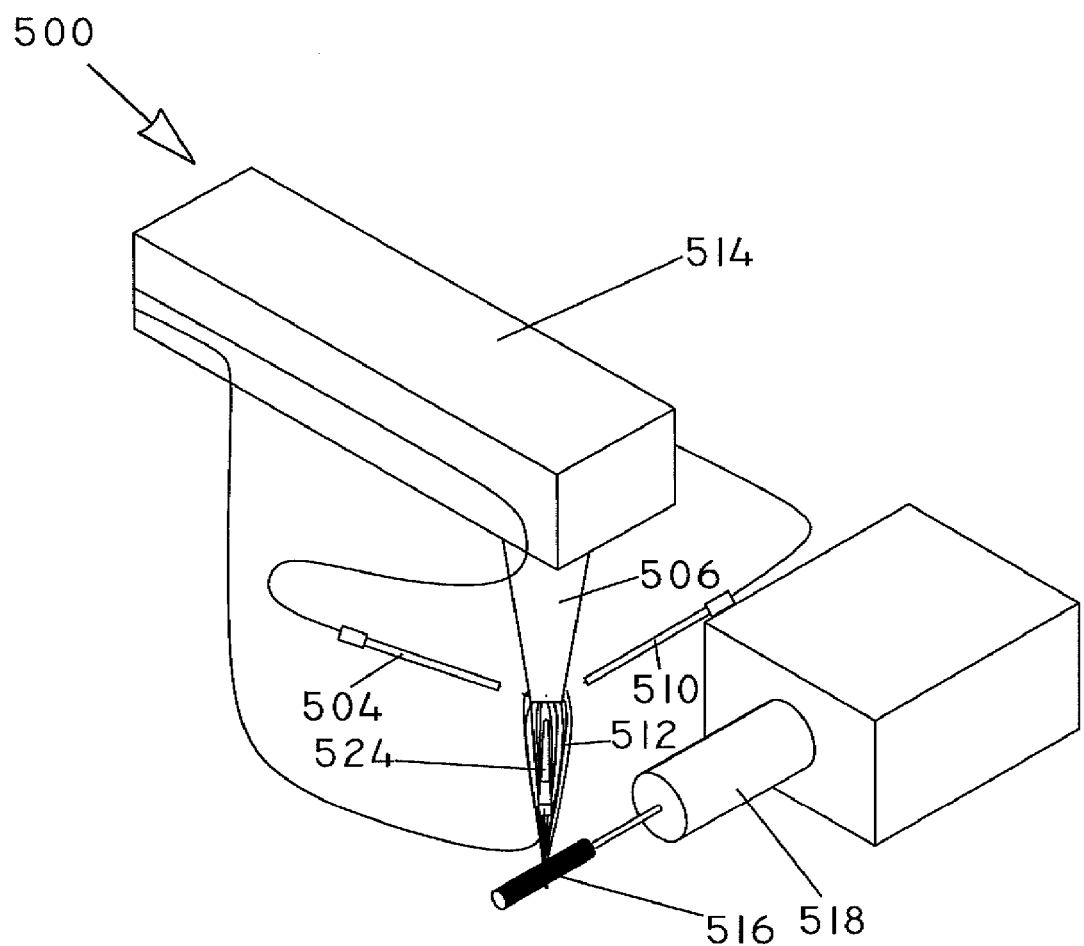
FIG. 6 is a schematic perspective view of a coating apparatus in accordance with another embodiment of the invention.

Embodiments of the spraying apparatus can also include those with more than two composition delivery conduits for each nozzle. Each different composition delivery conduit can supply a different coating composition or the same coating composition at a different concentration. As an example, FIG. 6 is a schematic perspective view of a coating apparatus 500 in accordance with another embodiment of the invention. In this view, a first composition delivery conduit 504 applies a first coating composition onto the nozzle 506. A second composition delivery conduit 510 applies a second coating composition onto the nozzle 506. A third composition delivery conduit 524 applies a third coating composition onto the nozzle 506. A spray stream 512 is generated by a nozzle 506 and is then applied to a medical device 516. The medical device 516 may be attached to a rotator device 518 in order to expose different sides of the medical device 516 to the spray stream 512. The nozzle 506 is connected to a sprayer arm 514 that can move the nozzle 506 as desired, such as back and forth or laterally. The first coating composition, the second coating composition, and the third coating composition can be the same or different. In an embodiment, the first coating composition, the second coating composition, and the third coating composition are different.

Figure 7:
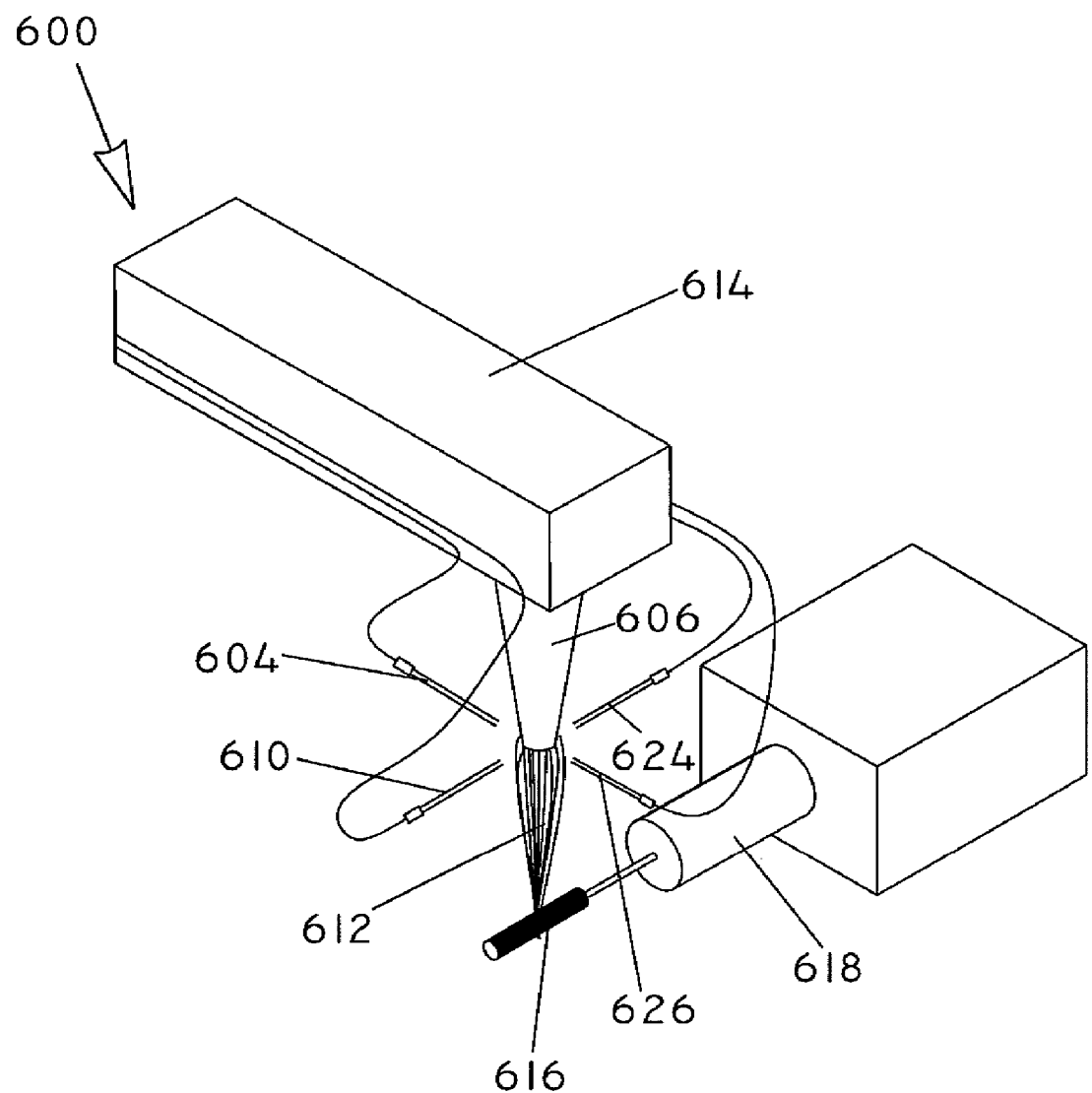
FIG. 7 is a schematic perspective view of a coating apparatus in accordance with another embodiment of the invention.

As a further example, FIG. 7 is a schematic perspective view of a coating apparatus 600 in accordance with another embodiment of the invention. In this view, a first composition delivery conduit 604 applies a first coating composition onto a nozzle 606. A second composition delivery conduit 610 applies a second coating composition onto the nozzle 606. A third composition delivery conduit 624 applies a third coating composition onto the nozzle 606. A fourth composition delivery conduit 626 applies a fourth coating composition onto the nozzle 606. A spray stream 612 is generated by a nozzle 606 and is then applied to a medical device 616. The medical device 616 may be attached to a rotator device 618 in order to expose different sides of the medical device 616 to the spray stream 612. However, it will be appreciated that the medical device 616 can be held with any suitable device holder or roller. The nozzle 606 is connected to a sprayer arm 614 that can move the nozzle 606 as desired, such as back and forth or laterally. The first coating composition, second coating composition, third coating composition, and fourth coating composition can be the same or different. In an embodiment, the first coating composition, the second coating composition, the third coating composition, and the fourth coating composition are different.

Figure 8:
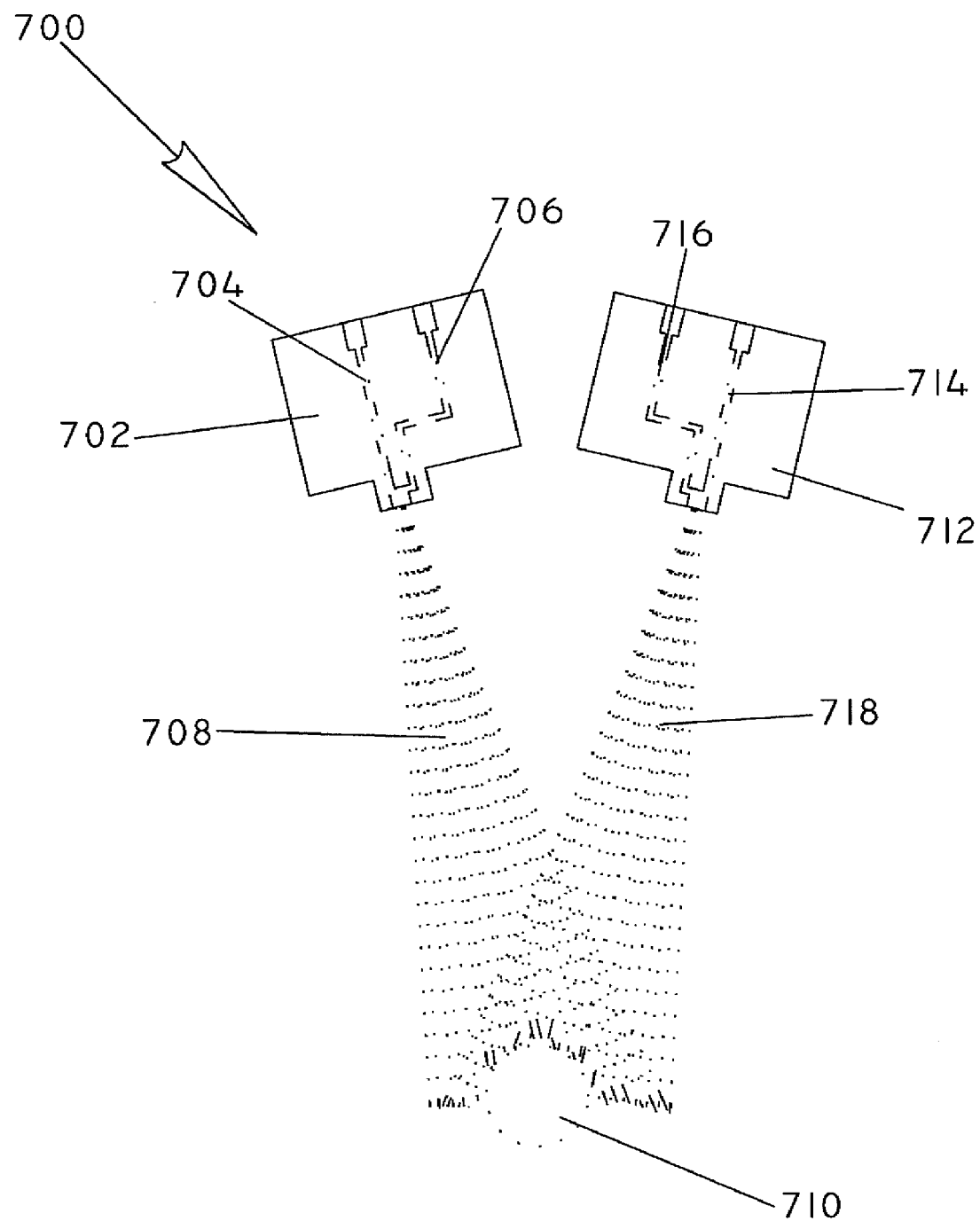
FIG. 8 is a schematic side view of another coating apparatus in accordance with an embodiment of the invention.

FIG. 8 is a schematic side view of a coating apparatus 700 in accordance with another embodiment of the invention. In this view, there is a first spray nozzle 702 and a second spray nozzle 712. Spray nozzles 702 and 712 are of the type that atomizes the coating composition using a flow of gas through the nozzle (gas-atomization type). By way of example, spray nozzle 702 has a composition delivery channel 704 that can be connected to a first composition delivery line (not shown). The nozzle 702 also includes a gas delivery channel 706 that can be connected to a first gas delivery line (not shown). The composition delivery channel 704 and gas delivery channel 706 can be provided as separate channels that are joined within the nozzle 702, so that the gas and composition are delivered from the nozzle 702 through a single opening. A suitable opening is approximately 0.040 inches (or about 1.016 mm) in some embodiments of the invention. However, it will be appreciated that various size openings can be used.

The gas is provided at sufficient pressure to provide sufficient atomization of the coating composition. Different types of gases can be used. In many embodiments, the gas is inert, such as nitrogen. An example of a suitable nozzle of this type is the SONICAIR nozzle, commercially available from Ivek Corporation (North Springfield, Vt.). Similarly, spray nozzle 712 has a composition delivery channel 714 that can be connected to a second composition delivery line (not shown). Spray nozzle 712 also includes a gas delivery channel 716 that can be connected to a second gas delivery line (not shown).

Spray nozzle 702 creates a first spray stream 708 and spray nozzle 712 creates a second spray stream 718. Both the first spray stream 708 and the second spray stream 718 are deposited onto a substrate 710, such as a medical device, simultaneously. In this embodiment, the two coating compositions forming the first and second spray streams (708 and 718) do not contact each other until their respective spray streams meet.

Figure 9:
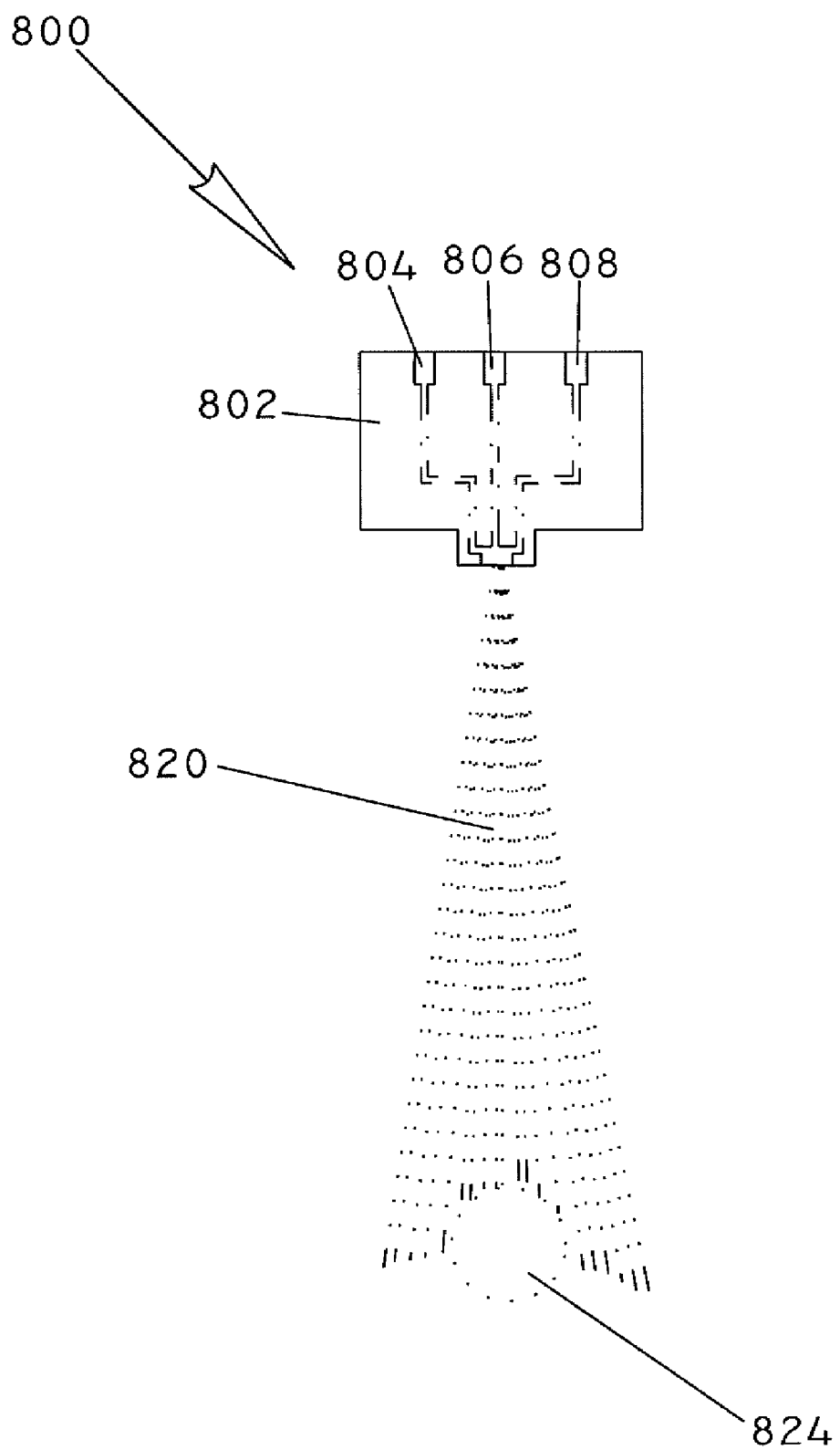
FIG. 9 is a schematic side view of another coating apparatus in accordance with an embodiment of the invention.

FIG. 9 is a schematic side view of another coating apparatus 800 in accordance with an embodiment of the invention. In this view, there is a spray nozzle 802 that is a gas-atomization type nozzle. Spray nozzle 802 has a first composition delivery channel 804 that can be connected to a first composition delivery line (not shown) and a second composition delivery channel 808 that can be connected to a second composition delivery line (not shown). The nozzle 802 also includes a gas delivery channel 806 that can be connected to a gas delivery line (not shown). The composition delivery channels 804 and 808 and gas delivery channel 806 can be provided as separate channels that are joined within the nozzle 802, so that the gas and composition are delivered from the nozzle 802 through a single opening. In this configuration, the contents of the first composition delivery channel 804 and the second composition delivery channel 808 are kept separate until gas atomization occurs. In operation, spray nozzle 802 creates a spray stream 820. Spray stream 820 is deposited onto a substrate 824, such as a medical device.

While not intending to be bound by theory, it is believed that ultrasonic-atomization spray nozzles (such as those shown in FIGS. 1-7) can offer advantages over gas-atomization spray nozzles (such as those shown in FIGS. 8-9). Specifically, ultrasonic-atomization type spray nozzles can be operated using less solvent per unit amount of polymer or active agent in comparison to gas-atomization type spray nozzles. It is believed that using less solvent can reduce issues associated with phase separation, such as where incompatible solvents and/or incompatible components are used to form the coating. Specifically, it is believed that using less solvent can reduce phase separation issues that could arise as the coating is applied on to the surface of a device.

Various other aspects of the invention will now be described in greater detail.

Polymers

Coating compositions used in embodiments of the invention can include one or more polymers. In an embodiment, the coating composition includes a plurality of polymers, including a first polymer and a second polymer. When the coating composition contains only one polymer, it can be either a first or second polymer as described herein. As used herein, term "(meth)acrylate" when used in describing polymers shall mean the form including the methyl group (methacrylate) or the form without the methyl group (acrylate).

Examples of suitable first polymers include poly(alkyl (meth)acrylates), and in particular, those with alkyl chain lengths from 2 to 8 carbons, and with molecular weights from 50 kilodaltons to 900 kilodaltons. An exemplary first polymer is poly(n-butyl methacrylate) (pBMA). Such polymers are available commercially, e.g., from Aldrich, with molecular weights ranging from about 200,000 Daltons to about 320,000 Daltons, and with varying inherent viscosity, solubility, and form (e.g., as crystals or powder).

Examples of suitable first polymers also include polymers selected from the group consisting of poly(aryl(meth)acrylates), poly(aralkyl (meth)acrylates), and poly(aryloxyalkyl (meth)acrylates). Such terms are used to describe polymeric structures wherein at least one carbon chain and at least one aromatic ring are combined with acrylic groups, typically esters, to provide a composition. In particular, exemplary polymeric structures include those with aryl groups having from 6 to 16 carbon atoms and with weight average molecular weights from about 50 to about 900 kilodaltons. Suitable poly(aralkyl(meth)acrylates), poly(arylalky(meth)acrylates) or poly(aryloxyalkyl (meth)acrylates) can be made from aromatic esters derived from alcohols also containing aromatic moieties. Examples of poly(aryl(meth)acrylates) include poly(9-anthracenyl methacrylate), poly(chlorophenylacrylate), poly(methacryloxy-2-hydroxybenzophenone), poly(methacryloxybenzotriazole), poly(naphthylacrylate) and -methacrylate), poly(4-nitrophenyl acrylate), poly(pentachloro(bromo, fluoro) acrylate) and -methacrylate), and poly(phenyl acrylate) and -methacrylate). Examples of poly(aralkyl (meth)acrylates) include poly(benzyl acrylate) and -methacrylate), poly(2-phenethyl acrylate) and -methacrylate), and poly(1-pyrenylmethyl methacrylate). Examples of poly(aryloxyalkyl (meth)acrylates) include poly(phenoxyethyl acrylate) and -methacrylate), and poly(polyethylene glycol phenyl ether acrylates) and -methacrylates) with varying polyethylene glycol molecular weights.

Examples of suitable second polymers are available commercially and include poly(ethylene-co-vinyl acetate) (PEVA) having vinyl acetate concentrations of between about 10% and about 50%, in the form of beads, pellets, granules, etc. pEVA co-polymers with lower percent vinyl acetate become increasingly insoluble in typical solvents, whereas those with higher percent vinyl acetate become decreasingly durable.

An exemplary polymer mixture for use in this invention includes mixtures of pBMA and pEVA. This mixture of polymers can be used with absolute polymer concentrations (i.e., the total combined concentrations of both polymers in the coating material), of between about 0.25 wt. % and about 99 wt. %. This mixture can also be used with individual polymer concentrations in the coating composition of between about 0.05 wt. % and about 99 wt. %. In one embodiment the polymer mixture includes pBMA with a molecular weight of from 100 kilodaltons to 900 kilodaltons and a pEVA copolymer with a vinyl acetate content of from 24 to 36 weight percent. In an embodiment the polymer mixture includes pBMA with a molecular weight of from 200 kilodaltons to 400 kilodaltons and a pEVA copolymer with a vinyl acetate content of from 24 to 36 weight percent. The concentration of the active agent or agents dissolved or suspended in the coating mixture can range from 0.01 to 99 percent, by weight, based on the weight of the final coating material.

Second polymers of the invention can also comprise one or more polymers selected from the group consisting of (i) poly(alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers. First polymers of the invention can also comprise a polymer selected from the group consisting of poly(alkyl (meth)acrylates) and poly(aromatic (meth)acrylates), where "(meth)" will be understood by those skilled in the art to include such molecules in either the acrylic and/or methacrylic form (corresponding to the acrylates and/or methacrylates, respectively).

Poly(alkylene-co-alkyl(meth)acrylates) include those copolymers in which the alkyl groups are either linear or branched, and substituted or unsubstituted with non-interfering groups or atoms. Such alkyl groups can comprise from 1 to 8 carbon atoms, inclusive. Such alkyl groups can comprise from 1 to 4 carbon atoms, inclusive. In an embodiment, the alkyl group is methyl. In some embodiments, copolymers that include such alkyl groups can comprise from about 15% to about 80% (wt) of alkyl acrylate. When the alkyl group is methyl, the polymer contains from about 20% to about 40% methyl acrylate in some embodiments, and from about 25% to about 30% methyl acrylate in a particular embodiment. When the alkyl group is ethyl, the polymer contains from about 15% to about 40% ethyl acrylate in an embodiment, and when the alkyl group is butyl, the polymer contains from about 20% to about 40% butyl acrylate in an embodiment.

Alternatively, second polymers for use in this invention can comprise ethylene copolymers with other alkylenes, which in turn, can include straight and branched alkylenes, as well as substituted or unsubstituted alkylenes. Examples include copolymers prepared from alkylenes that comprise from 3 to 8 branched or linear carbon atoms, inclusive. In an embodiment, copolymers prepared from alkylene groups that comprise from 3 to 4 branched or linear carbon atoms, inclusive. In a particular embodiment, copolymers prepared from alkylene groups containing 3 carbon atoms (e.g., propene). By way of example, the other alkylene is a straight chain alkylene (e.g., 1-alkylene). Exemplary copolymers of this type can comprise from about 20% to about 90% (based on moles) of ethylene. In an embodiment, copolymers of this type comprise from about 35% to about 80% (mole) of ethylene. Such copolymers will have a molecular weight of between about 30 kilodaltons to about 500 kilodaltons. Exemplary copolymers are selected from the group consisting of poly(ethylene-co-propylene), poly(ethylene-co-1-butene), polyethylene-co-1-butene-co-1-hexene) and/or poly(ethylene-co-1-octene).

"Polybutenes" suitable for use in the present invention include polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio. In an embodiment, the polybutene contains at least about 90% (wt) of isobutylene or 1-butene. In a particular embodiment, the polybutene contains at least about 90% (wt) of isobutylene. The polybutene may contain non-interfering amounts of other ingredients or additives, for example it can contain up to 1000 ppm of an antioxidant (e.g., 2,6-di-tert-butyl-methylphenol). By way of example, the polybutene can have a molecular weight between about 150 kilodaltons and about 1,000 kilodaltons. In an embodiment, the polybutene can have between about 200 kilodaltons and about 600 kilodaltons. In a particular embodiment, the polybutene can have between about 350 kilodaltons and about 500 kilodaltons. Polybutenes having a molecular weight greater than about 600 kilodaltons, including greater than 1,000 kilodaltons are available but are expected to be more difficult to work with.

Additional alternative second polymers include diolefin-derived, non-aromatic polymers and copolymers, including those in which the diolefin monomer used to prepare the polymer or copolymer is selected from butadiene ($CH_2$=CH—CH=$CH_2$) and/or isoprene ($CH_2$=C($CH_3$)CH=$CH_2$). In an embodiment, the polymer is a homopolymer derived from diolefin monomers or is a copolymer of diolefin monomer with non-aromatic mono-olefin monomer, and optionally, the homopolymer or copolymer can be partially hydrogenated. Such polymers can be selected from the group consisting of polybutadienes prepared by the polymerization of cis-, trans- and/or 1,2-monomer units, or from a mixture of all three monomers, and polyisoprenes prepared by the polymerization of cis-1,4- and/or trans-1,4-monomer units. Alternatively, the polymer is a copolymer, including graft copolymers, and random copolymers based on a non-aromatic mono-olefin monomer such as acrylonitrile, and an alkyl (meth)acrylate and/or isobutylene. In an embodiment, when the mono-olefin monomer is acrylonitrile, the interpolymerized acrylonitrile is present at up to about 50% by weight; and when the mono-olefin monomer is isobutylene, the diolefin is isoprene (e.g., to form what is commercially known as a "butyl rubber"). Exemplary polymers and copolymers have a molecular weight between about 150 kilodaltons and about 1,000 kilodaltons. In an embodiment, polymers and copolymers have a molecular weight between about 200 kilodaltons and about 600 kilodaltons.

Additional alternative second polymers include aromatic group-containing copolymers, including random copolymers, block copolymers and graft copolymers. In an embodiment, the aromatic group is incorporated into the copolymer via the polymerization of styrene. In a particular embodiment, the random copolymer is a copolymer derived from copolymerization of styrene monomer and one or more monomers selected from butadiene, isoprene, acrylonitrile, a $C_1$-$C_4$ alkyl (meth)acrylate (e.g., methyl methacrylate) and/or butene. Useful block copolymers include copolymer containing (a) blocks of polystyrene, (b) blocks of an polyolefin selected from polybutadiene, polyisoprene and/or polybutene (e.g., isobutylene), and (c) optionally a third monomer (e.g., ethylene) copolymerized in the polyolefin block. The aromatic group-containing copolymers contain about 10% to about 50% (wt.) of polymerized aromatic monomer and the molecular weight of the copolymer is from about 300 kilodaltons to about 500 kilodaltons. In an embodiment, the molecular weight of the copolymer is from about 100 kilodaltons to about 300 kilodaltons.

Additional alternative second polymers include epichlorohydrin homopolymers and poly(epichlorohydrin-co-alkylene oxide) copolymers. In an embodiment, in the case of the copolymer, the copolymerized alkylene oxide is ethylene oxide. By way of example, epichlorohydrin content of the epichlorohydrin-containing polymer is from about 30% to 100% (wt). In an embodiment, epichlorohydrin content is from about 50% to 100% (wt). In an embodiment, the epichlorohydrin-containing polymers have a molecular weight from about 100 kilodaltons to about 300 kilodaltons.

Polymers used in embodiments of the invention can also include those described in U.S. Pat. App. No. 60/703,555, entitled "DEVICES, ARTICLES, COATINGS, AND METHODS FOR CONTROLLED ACTIVE AGENT RELEASE OR HEMOCOMPATIBILITY", the contents of which is herein incorporated by reference. As a specific example, non-degradable polymers can include random copolymers of butyl methacrylate-co-acrylamido-methylpropane sulfonate (BMA-AMPS). In some embodiments, the random copolymer can include AMPS in an amount equal to about 0.5 mol. % to about 40 mol. %.

In an embodiment, polymers of the invention include hydrophobic polymers. One method of defining the hydrophobicity of a polymer is by the solubility parameter (or Hildebrand parameter) of the polymer. The solubility parameter describes the attractive strength between molecules of the material. The solubility parameter is represented by Equation 1:

$$\delta = (\Delta E^v/V)^{1/2} \quad \text{(Equation 1)}$$

where δ=solubility parameter ((cal/cm³)^{1/2})
ΔE^v=energy of vaporization (cal)
V=molar volume (cm³)

Solubility parameters cannot be calculated for polymers from heat of vaporization data because of their nonvolatility. Accordingly, solubility parameters must be calculated indirectly. One method involves identifying solvents in which a polymer dissolves without a change in heat or volume and then defining the solubility parameter of the polymer to be the same as the solubility parameters of the identified solvents. A more complete discussion of solubility parameters and methods of calculating the same can be found in Brandup et al., *Polymer Handbook*, 4th Ed., John Wiley & Sons, N.Y. (1999) beginning at VII p. 675.

As a general rule, the value of the solubility parameter δ is inversely proportional to the degree of hydrophobicity of a polymer. Thus, polymers that are very hydrophobic may have a low solubility parameter value. This general proposition is particularly applicable for polymers having a glass transition temperature below physiological temperature. In an embodiment, polymers used with the invention have a solubility parameter less than about 11.0 (cal/cm³)^{1/2}. In an embodiment polymers used with the invention have a solubility parameter of less than about 10.0 (cal/cm³)^{1/2}.

Polymers of the invention can include degradable (or biodegradable) polymers including both synthetic and natural polymers. Synthetic degradable polymers can include: degradable polyesters (such as poly(glycolic acid), poly(lactic acid), poly(lactic-co-glycolic acid), poly(dioxanone), polylactones (e.g., poly(caprolactone)), poly(3-hydroxybutyrate), poly(3-hydroxyvalerate), poly(valerolactone), poly(tartronic acid), poly(B-malonic acid), poly(propylene fumarate)); degradable polyesteramides; degradable polyanhydrides (such as poly(sebacic acid), poly(1,6-bis(carboxyphenoxy)hexane, poly(1,3-bis(carboxyphenoxy)propane); degradable polycarbonates; degradable polyiminocarbonates; degradable polyarylates; degradable polyorthoesters; degradable polyurethanes; degradable polyphosphazenes; and degradable polyhydroxyalkanoates; and copolymers thereof.

Natural or naturally-based degradable polymers can include polysaccharides and modified polysaccharides such as starch, cellulose, chitin, chitosan, and copolymers thereof.

Specific examples of degradable polymers include poly(ether ester) multiblock copolymers based on poly(ethylene glycol) (PEG) and poly(butylene terephthalate) that can be described by the following general structure:

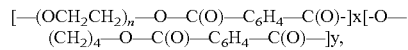

where —C₆H₄— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer. n can be selected such that the molecular weight of the PEG block is between about 300 and about 4000. X and y can be selected so that the multiblock copolymer contains from about 55% up to about 80% PEG by weight. The block copolymer can be engineered to provide a wide array of physical characteristics (e.g., hydrophilicity, adherence, strength, malleability, degradability, durability, flexibility) and active agent release characteristics (e.g., through controlled polymer degradation and swelling) by varying the values of n, x and y in the copolymer structure.

Degradable polyesteramides can include those formed from the monomers OH-x-OH, z, and COOH-y-COOH, wherein x is alkyl, y is alkyl, and z is valine, leucine, isoleucine, norleucine, methionine, or phenylalanine.

Degradable polymeric materials can also be selected from: (a) non-peptide polyamino polymers; (b) polyiminocarbonates; (c) polycarbonates and polyarylates; and (d) poly(alkylene oxide) polymers.

In an embodiment, the degradable polymeric material is composed of a non-peptide polyamino acid polymer. Exemplary non-peptide polyamino acid polymers are described, for example, in U.S. Pat. No. 4,638,045 ("Non-Peptide Polyamino Acid Bioerodible Polymers," Jan. 20, 1987). Generally speaking, these polymeric materials are derived from monomers, including two or three amino acid units having one of the following two structures illustrated below:

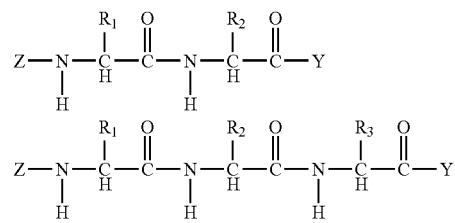

wherein the monomer units are joined via hydrolytically labile bonds at not less than one of the side groups R₁, R₂, and R₃, and where R₁, R₂, R₃ are the side chains of naturally occurring amino acids; Z is any desirable amine protecting group or hydrogen; and Y is any desirable carboxyl protecting group or hydroxyl. Each monomer unit comprises naturally occurring amino acids that are then polymerized as monomer units via linkages other than by the amide or "peptide" bond. The monomer units can be composed of two or three amino acids united through a peptide bond and thus comprise dipeptides or tripeptides. Regardless of the precise composition of the monomer unit, all are polymerized by hydrolytically labile bonds via their respective side chains rather than via the amino and carboxyl groups forming the amide bond typical of polypeptide chains. Such polymer compositions are non-toxic, are degradable, and can provide zero-order release kinetics for the delivery of active agents in a variety of therapeutic applications. According to these aspects, the amino acids are selected from naturally occurring L-alpha amino acids, including alanine, valine, leucine, isoleucine, proline, serine, threonine, aspartic acid, glutamic acid, asparagine, glutamine, lysine, hydroxylysine, arginine, hydroxyproline, methionine, cysteine, cystine, phenylalanine, tyrosine, tryptophan, histidine, citrulline, ornithine, lanthionine, hypoglycin A, β-alanine, γ-amino butyric acid, α aminoadipic acid, canavanine, venkolic acid, thiolhistidine, ergothionine, dihydroxyphenylalanine, and other amino acids well recognized and characterized in protein chemistry.

In an embodiment, the degradable polymeric material can be composed of polyiminocarbonates. Polyiminocarbonates are structurally related to polycarbonates, wherein imino groups (C=NH) are present in the places normally occupied by carbonyl oxygen in the polycarbonates. Thus, the degradable component can be formed of polyiminocarbonates having linkages

For example, one useful polyiminocarbonate has the general polymer structural formula

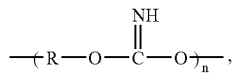

wherein R is an organic divalent group containing a non-fused aromatic organic ring, and n is greater than 1. Embodiments of the R group within the general formula above are exemplified by, but is not limited to, the following:

R group

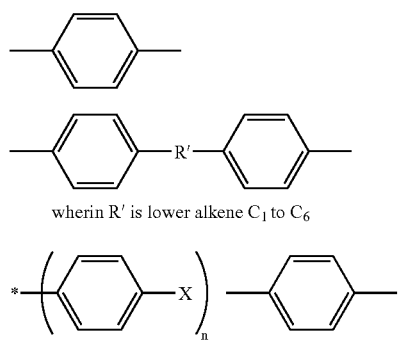

wherein n is an interger equal to or greater than 1, X is a hetero atom such as —O—, —S—, or a bridging group such as —NH—, —S(=O)—, —SO$_2$—, —C(=O)—, —C(CH$_3$)$_2$—, —CH(CH$_3$)—, —CH(CH$_3$)—CH$_2$—CH(CH$_3$)—, Also, compounds of the general formula

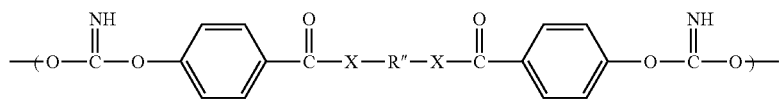

can be utilized, wherein X is O, NH, or NR'", wherein R'" is a lower alkyl radical; and R" is a divalent residue of a hydrocarbon including polymers such as a polyolefin, an oligoglycol or polyglycol such as polyalkylene glycol ether, a polyester, a polyurea, a polyamine, a polyurethane, or a polyamide. Exemplary starting material for use in accordance with these embodiments include diphenol compounds having the formula

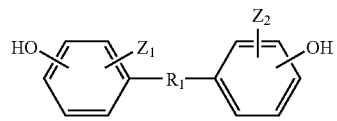

and dicyanate compounds having the formula

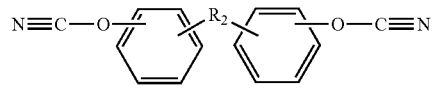

with $R_1$ and $R_2$ being the same or different and being alkylene, arylene, alkylarylene or a functional group containing heteroatoms. $Z_1$, and $Z_2$ can each represent one or more of the same or different radicals selected from the group consisting of hydrogen, halogen, lower-alkyl, carboxyl, amino, nitro, thioether, sulfoxide, and sulfonyl. Each of $Z_1$ and $Z_2$ can be hydrogen.

Degradable polymers of the invention can also include polymerized polysaccharides such as those described in U.S. Pub. App. No. US 2005/0255142, entitled "COATINGS FOR MEDICAL ARTICLES INCLUDING NATURAL BIODEGRADABLE POLYSACCHARIDES", U.S. application Ser. No. 11/271,213, entitled "COATINGS INCLUDING NATURAL BIODEGRADABLE POLYSACCHARIDES AND USES THEREOF", and in U.S. Application No. 60/782,957, entitled "HYDROPHOBIC DERIVATIVES OF NATURAL BIODEGRADABLE POLYSACCHARIDES", all of which are herein incorporated by reference.

Degradable polymers of the invention can also include dextran based polymers such as those described in U.S. Pat. No. 6,303,148, entitled "PROCESS FOR THE PREPARATION OF A CONTROLLED RELEASE SYSTEM". Exemplary dextran based degradable polymers including those available commercially under the trade name OCTODEX. Degradable polymers of the invention can further include collagen/hyaluronic acid polymers.

Active Agents

Coating compositions used with methods of the invention can contain one or more active agents. As used herein, the term "active agent" means a compound that has a particular desired activity. For example, an active agent can be a therapeutic compound that exerts a specific activity on a subject. In some embodiments, active agent will, in turn, refer to a peptide, protein, carbohydrate, nucleic acid, lipid, polysaccharide or combinations thereof, or synthetic inorganic or organic molecule, that causes a desired biological effect when administered in vivo to an animal, including but not limited to birds and mammals, including humans. In some embodiments, the active agent can be a bioactive agent. Active agents can have many different types of elution profiles.

Active agents useful according to the invention include substances that possess desirable therapeutic characteristics for application to the implantation site. Active agents useful in the present invention can include many types of therapeutics including thrombin inhibitors, antithrombogenic agents, thrombolytic agents, fibrinolytic agents, anticoagulants, anti-platelet agents, vasospasm inhibitors, calcium channel blockers, steroids, vasodilators, anti-hypertensive agents, antimicrobial agents, antibiotics, antibacterial agents, antiparasite and/or antiprotozoal solutes, antiseptics, antifungals, angiogenic agents, anti-angiogenic agents, inhibitors of surface glycoprotein receptors, antimitotics, microtubule inhibitors, antisecretory agents, actin inhibitors, remodeling inhibitors, antisense nucleotides, anti-metabolites, miotic agents, anti-proliferatives, anticancer chemotherapeutic agents, anti-neoplastic agents, antipolymerases, antivirals, anti-AIDS substances, anti-inflammatory steroids or non-steroidal anti-inflammatory agents, analgesics, antipyretics, immunosuppressive agents, immunomodulators, growth hormone antagonists, growth factors, radiotherapeutic agents, peptides, proteins, enzymes, extracellular matrix components, ACE inhibitors, free radical scavengers, chelators, antioxidants, photodynamic therapy agents, gene therapy agents, anesthetics, immunotoxins, neurotoxins, opioids, dopamine agonists, hypnotics, antihistamines, tranquilizers, anticonvulsants, muscle relaxants and anti-Parkinson substances, antispasmodics and muscle contractants, anticholinergics, ophthalmic agents, antiglaucoma solutes, prostaglandins, antidepressants, antipsychotic substances, neurotransmitters, anti-emetics, imaging agents, specific targeting agents, and cell response modifiers.

More specifically, in embodiments the active agent can include heparin, covalent heparin, synthetic heparin salts, or another thrombin inhibitor; hirudin, hirulog, argatroban, D-phenylalanyl-L-poly-L-arginyl chloromethyl ketone, or another antithrombogenic agent; urokinase, streptokinase, a tissue plasminogen activator, or another thrombolytic agent; a fibrinolytic agent; a vasospasm inhibitor; a calcium channel blocker, a nitrate, nitric oxide, a nitric oxide promoter, nitric oxide donors, dipyridamole, or another vasodilator; HYTRIN® or other antihypertensive agents; a glycoprotein IIb/IIIa inhibitor (abciximab) or another inhibitor of surface glycoprotein receptors; aspirin, ticlopidine, clopidogrel or another antiplatelet agent; colchicine or another antimitotic, or another microtubule inhibitor; dimethyl sulfoxide (DMSO), a retinoid, or another antisecretory agent; cytochalasin or another actin inhibitor; cell cycle inhibitors; remodeling inhibitors; deoxyribonucleic acid, an antisense nucleotide, or another agent for molecular genetic intervention; methotrexate, or another antimetabolite or antiproliferative agent; tamoxifen citrate, TAXOL®, paclitaxel, or the derivatives thereof, rapamycin (or other rapalogs e.g. ABT-578 or sirolimus), vinblastine, vincristine, vinorelbine, etoposide, tenopiside, dactinomycin (actinomycin D), daunorubicin, doxorubicin, idarubicin, anthracyclines, mitoxantrone, bleomycin, plicamycin (mithramycin), mitomycin, mechlorethamine, cyclophosphamide and its analogs, chlorambucil, ethylenimines, methylmelamines, alkyl sulfonates (e.g., busulfan), nitrosoureas (carmustine, etc.), streptozocin, methotrexate (used with many indications), fluorouracil, floxuridine, cytarabine, mercaptopurine, thioguanine, pentostatin, 2-chlorodeoxyadenosine, cisplatin, carboplatin, procarbazine, hydroxyurea, morpholino phosphorodiamidate oligomer or other anti-cancer chemotherapeutic agents; cyclosporin, tacrolimus (FK-506), pimecrolimus, azathioprine, mycophenolate mofetil, mTOR inhibitors, or another immunosuppressive agent; cortisol, cortisone, dexamethasone, dexamethasone sodium phosphate, dexamethasone acetate, dexamethasone derivatives, betamethasone, fludrocortisone, prednisone, prednisolone, 6U-methylprednisolone, triamcinolone (e.g., triamcinolone acetonide), or another steroidal agent; trapidil (a PDGF antagonist), angiopeptin (a growth hormone antagonist), angiogenin, a growth factor (such as vascular endothelial growth factor (VEGF)), or an anti-growth factor antibody (e.g., ranibizumab, which is sold under the tradename LUCENTIS®, or another growth factor antagonist or agonist; dopamine, bromocriptine mesylate, pergolide mesylate, or another dopamine agonist; $^{60}$Co (5.3 year half life), $^{192}$Ir (73.8 days), $^{32}$P (14.3 days), $^{111}$In (68 hours), $^{90}$Y (64 hours), $^{99}$Tc (6 hours), or another radiotherapeutic agent; iodine-containing compounds, barium-containing compounds, gold, tantalum, platinum, tungsten or another heavy metal functioning as a radiopaque agent; a peptide, a protein, an extracellular matrix component, a cellular component or another biologic agent; captopril, enalapril or another angiotensin converting enzyme (ACE) inhibitor; angiotensin receptor blockers; enzyme inhibitors (including growth factor signal transduction kinase inhibitors); ascorbic acid, alpha tocopherol, superoxide dismutase, deferoxamine, a 21-aminosteroid (lasaroid) or another free radical scavenger, iron chelator or antioxidant; a $^{14}$C—, $^{3}$H—, $^{131}$I—, $^{32}$P— or $^{36}$S-radiolabelled form or other radiolabelled form of any of the foregoing; an estrogen (such as estradiol, estriol, estrone, and the like) or another sex hormone; AZT or other antipolymerases; acyclovir, famciclovir, rimantadine hydrochloride, ganciclovir sodium, Norvir, Crixivan, or other antiviral agents; 5-aminolevulinic acid, meta-tetrahydroxyphenylchlorin, hexadecafluorozinc phthalocyanine, tetramethyl hematoporphyrin, rhodamine 123 or other photodynamic therapy agents; an IgG2 Kappa antibody against *Pseudomonas aeruginosa* exotoxin A and reactive with A431 epidermoid carcinoma cells, monoclonal antibody against the noradrenergic enzyme dopamine beta-hydroxylase conjugated to saporin, or other antibody targeted therapy agents; gene therapy agents; enalapril and other prodrugs; PROSCAR®, HYTRIN® or other agents for treating benign prostatic hyperplasia (BHP); mitotane, aminoglutethimide, breveldin, acetaminophen, etodalac, tolmetin, ketorolac, ibuprofen and derivatives, mefenamic acid, meclofenamic acid, piroxicam, tenoxicam, phenylbutazone, oxyphenbutazone, nabumetone, auranofin, aurothioglucose, gold sodium thiomalate, a mixture of any of these, or derivatives of any of these.

Other biologically useful compounds that can also be included in the coating include, but are not limited to, hormones, β-blockers, anti-anginal agents, cardiac inotropic agents, corticosteroids, analgesics, anti-inflammatory agents, anti-arrhythmic agents, immunosuppressants, anti-bacterial agents, anti-hypertensive agents, anti-malarials, anti-neoplastic agents, anti-protozoal agents, anti-thyroid agents, sedatives, hypnotics and neuroleptics, diuretics, anti-parkinsonian agents, gastro-intestinal agents, anti-viral agents, anti-diabetics, anti-epileptics, anti-fungal agents, histamine H-receptor antagonists, lipid regulating agents, muscle relaxants, nutritional agents such as vitamins and minerals, stimulants, nucleic acids, polypeptides, and vaccines.

Antibiotics are substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, erythromycin, geldanamycin, geldanamycin analogs, cephalosporins, or the like. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Antiseptics are recognized as substances that prevent or arrest the growth or action of microorganisms, generally in a nonspecific fashion, e.g., either by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Antiviral agents are substances capable of destroying or suppressing the replication of viruses. Examples of anti-viral agents include α-methyl-1-adamantanemethylamine, hydroxy-ethoxymethylguanine, adamantanamine, 5-iodo-2'-deoxyuridine, trifluorothymidine, interferon, and adenine arabinoside.

Enzyme inhibitors are substances that inhibit an enzymatic reaction. Examples of enzyme inhibitors include edrophonium chloride, N-methylphysostigmine, neostigmine bromide, physostigmine sulfate, tacrine HCL, tacrine, 1-hydroxy maleate, iodotubercidin, p-bromotetramisole, 10-(α-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylaminie, N-monomethyl-L-arginine acetate, carbidopa, 3-hydroxybenzylhydrazine HCl, hydralazine HCl, clorgyline HCl, deprenyl HCl L(−), deprenyl HCl D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-di-phenylvalerate hydrochloride, 3-isobutyl-1-methylxanthne, papaverine HCl, indomethacind, 2-cyclooctyl-2-hydroxyethylamine hydrochloride, 2,3-dichloro-α-methylbenzylamine (DCMB), 8,9-dichloro-2,3,4,5-tetrahydro-1H-2-benzazepine hydrochloride, p-aminoglutethimide, p-aminoglutethimide tartrate R(+), p-aminoglutethimide tartrate S(−), 3-iodotyrosine, alpha-methyltyrosine L(−), alpha-methyltyrosine D(−), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances that have an anesthetic effect in a localized region. Examples of such anesthetics include procaine, lidocaine, tetracaine and dibucaine.

Imaging agents are agents capable of imaging a desired site, e.g., tumor, in vivo. Examples of imaging agents include substances having a label that is detectable in vivo, e.g., antibodies attached to fluorescent labels. The term antibody includes whole antibodies or fragments thereof.

Cell response modifiers are chemotactic factors such as platelet-derived growth factor (PDGF). Other chemotactic factors include neutrophil-activating protein, monocyte chemoattractant protein, macrophage-inflammatory protein, SIS (small inducible secreted), platelet factor, platelet basic protein, melanoma growth stimulating activity, epidermal growth factor, transforming growth factor alpha, fibroblast growth factor, platelet-derived endothelial cell growth factor, insulin-like growth factor, nerve growth factor, bone growth/cartilage-inducing factor (alpha and beta), and matrix metalloproteinase inhibitors. Other cell response modifiers are the interleukins, interleukin receptors, interleukin inhibitors, interferons, including alpha, beta, and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins, antisense molecules, androgenic receptor blockers and statin agents.

Active agents used with the invention can include macromolecules, small molecules, hydrophilic molecules, hydrophobic molecules, and the like. Macromolecular active agents used with embodiments of the invention can include proteins, nucleic acids, and polysaccharides. By way of example, proteins can include glycosylated proteins, antibodies (both monoclonal and polyclonal), antibody derivatives (including diabodies, f(ab) fragments, humanized antibodies, etc.), cytokines, growth factors, receptor ligands, enzymes, and the like. Nucleic acids can include RNA, DNA, cDNA, and the like.

In an embodiment, macromolecular active agents used with the invention have a molecular weight (or average molecular weight) of greater than about 10 kD (1 kilodalton is equal to 1,000 atomic mass units). In an embodiment, the macromolecular active agent includes a protein of greater than about 10 kD. In an embodiment, the macromolecular active agent includes a protein of greater than about 100 kD.

In some embodiments, the active agent of the coating can include agents that are small molecules. In some embodiments, the active agent can include therapeutic agents that are hydrophilic small molecules. In some embodiments, the active agent can include therapeutic agents that are hydrophobic small molecules. As used herein, small molecules can include those with a molecular weight of equal to or less than 10 kilodaltons. In an embodiment, small molecules have a molecular weight of less than about 5 kilodaltons.

By way of example, small molecule active agents can include Trigonelline HCL, diclofenac, and chlorhexidine diacetate. Small molecules can include many types of therapeutics including those as described above with respect to macromolecules (e.g., thrombin inhibitors, antithrombogenic agents, etc.).

The weight of the coating attributable to the active agent can be in any range desired for a given active agent in a given application. In some embodiments, weight of the coating attributable to the active agent is in the range of about 1 microgram to about 10 milligrams of active agent per $cm^2$ of the effective surface area of the device. By "effective" surface area it is meant the surface amenable to being coated with the composition itself. For a flat, nonporous, surface, for instance, this will generally be the macroscopic surface area itself, while for considerably more porous or convoluted (e.g., corrugated, pleated, or fibrous) surfaces the effective surface area can be significantly greater than the corresponding macroscopic surface area. In an embodiment, the weight of the coating attributable to the active agent is between about 0.01 mg and about 0.5 mg of active agent per cm2 of the gross surface area of the device. In an embodiment, the weight of the coating attributable to the active agent is greater than about 0.01 mg.

In some embodiments, more than one active agent can be used as a part of the coating material. Specifically, co-agents or co-drugs can be used. A co-agent or co-drug can act differently than the first agent or drug. The co-agent or co-drug can have an elution profile that is different than the first agent or drug. In some embodiments, accessory agents are included such as chaperonins.

Solvents

As described above, one or more of the coating compositions used can include polymers. In an embodiment, coating compositions including polymers also include a polymer composition solvent. For example, one or more polymers can be combined with one or more polymer composition solvents to form a coating composition. It will be appreciated that a wide variety of solvents or combinations of solvents can be used, ranging from polar to nonpolar solvents depending on the particular polymer or polymers acting as the solute. Examples of polymer composition solvents can include water, alcohols (e.g., methanol, butanol, propanol, and isopropanol), alkanes (e.g., halogenated such as chloroform or unhalogenated alkanes such as hexane and cyclohexane), amides (e.g., dimethylformamide), ethers (e.g., THF and dioxolane), ketones (e.g., methylethylketone), aromatic compounds (e.g., toluene and xylene), nitriles (e.g., acetonitrile) and esters (e.g., ethyl acetate). In an embodiment, the polymer composition solvent is one in which a polymer component(s) forms a true solution. In some embodiments, the polymer composition solvent includes a component that is not miscible with water.

In an embodiment, the polymer composition solvent and/or the active agent composition solvent includes a combination of different solvents. It is believed that using a combination of solvents can affect the active agent elution rate, particularly where at least one of the solvent(s) used in the polymer composition and at least one solvent(s) in the active agent composition have incompatible solubility properties. For example, where chloroform is used as one solvent for the polymer(s) and water is used as a solvent for the active agent, adding an additional solvent to the polymer composition that is more polar than chloroform but less polar than water, such as methanol, can affect the resulting active agent elution profile. This effect is shown by comparing the elution rates in Example 1 below with the elution rates in Example 2 below. Specifically, Example 1, where a combination of chloroform and methanol was used as the polymer composition solvent, shows relatively slower elution rates of BSA than does Example 2, where only chloroform was used as the polymer composition solvent. Therefore, in some embodiments, at least three different solvents are used in total between the polymer composition and the active agent composition. In some embodiments, two different solvents are used in the polymer composition and one solvent is used in the active agent composition. In other embodiments, one solvent is used in the polymer composition and two solvents are used in the active agent composition.

In some embodiments, the polymer composition solvent can include from about 60% to about 98% by volume of a water immiscible component and from about 2% to about 40% by volume of a water miscible component. The water immiscible component can include chloroform or another non-polar solvent. The water miscible component can include an alcohol. In an embodiment, the water miscible component includes methanol. In an embodiment, the polymer composition solvent can include from about 70% to about 90% by volume chloroform and from about 10% to about 30% by volume methanol.

As described above, one or more of the coating compositions used can include active agent(s). In an embodiment, coating compositions including active agents also include an active agent composition solvent. For example, one or more active agents can be combined with one or more active agent composition solvents to form an active agent composition. It will be appreciated that a wide variety of solvents or combinations of solvents can be used, ranging from polar to nonpolar solvents depending on the particular active agent or active agents acting as the solute. Examples of active agent composition solvents can include water, alcohols (e.g., methanol, butanol, propanol, and isopropanol), alkanes (e.g., halogenated such as chloroform or unhalogenated alkanes such as hexane and cyclohexane), amides (e.g., dimethylformamide), ethers (e.g., THF and dioxolane), ketones (e.g., methylethylketone), aromatic compounds (e.g., toluene and xylene), nitriles (e.g., acetonitrile) and esters (e.g., ethyl acetate). In an embodiment, active agent solvents of the invention includes non-aqueous solvents. In an embodiment, active agent solvents of the invention includes aqueous solvents. In an embodiment, the active agent solvent of the invention can include the presence of salts. In an embodiment, the active agent solvent of the invention is phosphate buffered saline (PBS). Active agent solvents of the invention can also include combinations of solvents including polar solvents that are miscible with water.

In some embodiments, a component of the active agent solvent of the invention is substantially immiscible with a component of the polymer composition solvent. In an embodiment, the active agent solvent of the invention is immiscible with the polymer composition solvent to a degree such that two phases are formed when the two solvents are put into the same vessel.

Devices

Embodiments of the invention can be used to coat many different types of devices including medical devices. Medical devices can include both implantable devices and non-implantable medical devices.

Embodiments of the invention can be used with implantable, or transitorily implantable, devices including, but not limited to, vascular devices such as grafts (e.g., abdominal aortic aneurysm grafts, etc.), stents (e.g., self-expanding stents typically made from nitinol, balloon-expanded stents typically prepared from stainless steel, degradable coronary stents, etc.), catheters (including arterial, intravenous, blood pressure, stent graft, etc.), valves (e.g., polymeric or carbon mechanical valves, tissue valves, valve designs including percutaneous, sewing cuff, and the like), embolic protection filters (including distal protection devices), vena cava filters, aneurysm exclusion devices, artificial hearts, cardiac jackets, and heart assist devices (including left ventricle assist devices), implantable defibrillators, electro-stimulation devices and leads (including pacemakers, lead adapters and lead connectors), implanted medical device power supplies (e.g., batteries, etc.), peripheral cardiovascular devices, atrial septal defect closures, left atrial appendage filters, valve annuloplasty devices (e.g., annuloplasty rings), mitral valve repair devices, vascular intervention devices, ventricular assist pumps, and vascular access devices (including parenteral feeding catheters, vascular access ports, central venous access catheters); surgical devices such as sutures of all types, staples, anastomosis devices (including anastomotic closures), suture anchors, hemostatic barriers, screws, plates, clips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps; orthopedic devices such as joint implants, acetabular cups, patellar buttons, bone repair/augmentation devices, spinal devices (e.g., vertebral disks and the like), bone pins, cartilage repair devices, and artificial tendons; dental devices such as dental implants and dental fracture repair devices; drug delivery devices such as drug delivery pumps, implanted drug infusion tubes, drug infusion catheters, and intravitreal drug delivery devices; ophthalmic devices including orbital implants, glaucoma drain shunts and intraocular lenses; urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices; synthetic prostheses such as breast prostheses and artificial organs (e.g., pancreas, liver, lungs, heart, etc.); respiratory devices including lung catheters; neurological devices such as neurostimulators, neurological catheters, neurovascular balloon catheters, neuro-aneurysm treatment coils, and neuropatches; ear nose and throat devices such as nasal buttons, nasal and airway splints, nasal tampons, ear wicks, ear drainage tubes, tympanostomy vent tubes, otological strips, laryngectomy tubes, esophageal tubes, esophageal stents, laryngeal stents, salivary bypass tubes, and tracheostomy tubes; biosensor devices including glucose sensors, cardiac sensors, intra-arterial blood gas sensors; oncological implants; and pain management implants.

Classes of suitable non-implantable devices can include dialysis devices and associated tubing, catheters, membranes, and grafts; autotransfusion devices; vascular and surgical devices including atherectomy catheters, angiographic catheters, intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dialators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

In some aspects, embodiments of the invention can be utilized in connection with ophthalmic devices. Suitable ophthalmic devices in accordance with these aspects can provide bioactive agent to any desired area of the eye. In some aspects, the devices can be utilized to deliver bioactive agent to an anterior segment of the eye (in front of the lens), and/or a posterior segment of the eye (behind the lens). Suitable ophthalmic devices can also be utilized to provide bioactive agent to tissues in proximity to the eye, when desired.

In some aspects, embodiments of the invention can be utilized in connection with ophthalmic devices configured for placement at an external or internal site of the eye. Suitable external devices can be configured for topical administration of bioactive agent. Such external devices can reside on an external surface of the eye, such as the cornea (for example, contact lenses) or bulbar conjunctiva. In some embodiments, suitable external devices can reside in proximity to an external surface of the eye.

Devices configured for placement at an internal site of the eye can reside within any desired area of the eye. In some aspects, the ophthalmic devices can be configured for placement at an intraocular site, such as the vitreous. Illustrative intraocular devices include, but are not limited to, those described in U.S. Pat. No. 6,719,750 B2 ("Devices for Intraocular Drug Delivery," Varner et al.) and U.S. Pat. No. 5,466,233 ("Tack for Intraocular Drug Delivery and Method for Inserting and Removing Same," Weiner et al.); U.S. Publication Nos. 2005/0019371 A1 ("Controlled Release Bioactive Agent Delivery Device," Anderson et al.), 2004/0133155 A1 ("Devices for Intraocular Drug Delivery," Varner et al.), 2005/0059956 A1 ("Devices for Intraocular Drug Delivery," Varner et al.), and 2003/0014036 A1 ("Reservoir Device for Intraocular Drug Delivery," Varner et al.); and U.S. application Ser. No. 11/204,195 (filed Aug. 15, 2005, Anderson et al.), Ser. No. 11/204,271 (filed Aug. 15, 2005, Anderson et al.), Ser. No. 11/203,981 (filed Aug. 15, 2005, Anderson et al.), Ser. No. 11/203,879 (filed Aug. 15, 2005, Anderson et al.), Ser. No. 11/203,931 (filed Aug. 15, 2005, Anderson et al.); and related applications.

In some aspects, the ophthalmic devices can be configured for placement at a subretinal area within the eye. Illustrative ophthalmic devices for subretinal application include, but are not limited to, those described in U.S. Patent Publication No. 2005/0143363 ("Method for Subretinal Administration of Therapeutics Including Steroids; Method for Localizing Pharmacodynamic Action at the Choroid and the Retina; and Related Methods for Treatment and/or Prevention of Retinal Diseases," de Juan et al.); U.S. application Ser. No. 11/175,850 ("Methods and Devices for the Treatment of Ocular Conditions," de Juan et al.); and related applications.

Suitable ophthalmic devices can be configured for placement within any desired tissues of the eye. For example, ophthalmic devices can be configured for placement at a subconjunctival area of the eye, such as devices positioned extrasclerally but under the conjunctiva, such as glaucoma drainage devices and the like.

Substrates

Embodiments of the invention provide the ability to deliver active agents from a variety of substrate surfaces including metals, polymers, ceramics, and natural materials.

Metals include, but are not limited to, titanium, stainless steel, and cobalt chromium. Suitable metals can also include the noble metals such as gold, silver, copper, and platinum. Finally, suitable metals can include alloys such as nitinol or cobalt chromium alloys.

Polymers include those formed of synthetic polymers, including oligomers, homopolymers, and copolymers resulting from either addition or condensation polymerizations. Examples include, but not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, styrene, vinyl chloride, vinyl acetate, vinyl pyrrolidone, and vinylidene difluoride, condensation polymers including, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetheretherketone.

Embodiments of the invention can also include the use of ceramics as a substrate. The ceramics include, but are not limited to, silicon nitride, silicon carbide, zirconia, and alumina, as well as glass, silica, and sapphire.

Certain natural materials are also suitable including human tissue, when used as a component of a device, such as bone, cartilage, skin and teeth; and other organic materials such as wood, cellulose, compressed carbon, rubber, silk, wool, and cotton. The composition of the substrate can also include resins, polysaccharides, silicon, or silica-based materials, glass, films, gels, and membranes.

Coating Configurations

Embodiments of the invention include coatings produced by coating apparatus having multiple coating composition delivery conduits (or supply feed tubes). As an example, embodiments of the invention include coatings having a concentration gradient of a component (such as a first polymer) relative to one or more different components (such as a second polymer). Embodiments of the invention can include coatings having a concentration gradient of an active agent relative to one or more polymeric components.

The term "gradient", as used herein, shall refer to a change in concentration of a component, such as a polymer or active agent, with respect to change in depth or thickness of a coating. The term "continuous gradient", as used herein, shall refer to a gradient wherein the change in concentration of a component changes continuously, in contrast to changing in a stepped manner. The term "stepped gradient", as used herein, shall refer to a gradient wherein the change in concentration of a component changes in discrete amounts or quanta. Stepped gradients in embodiments of the invention can include a plurality of steps, wherein each step represents a region of substantially uniform concentration of one component with respect to another. In an embodiment, a stepped concentration gradient includes greater than two steps. In an embodiment, a stepped concentration gradient includes greater than three steps. In an embodiment, a stepped concentration gradient includes greater than five steps. In an embodiment, a stepped concentration gradient includes greater than ten steps.

Figure 10:
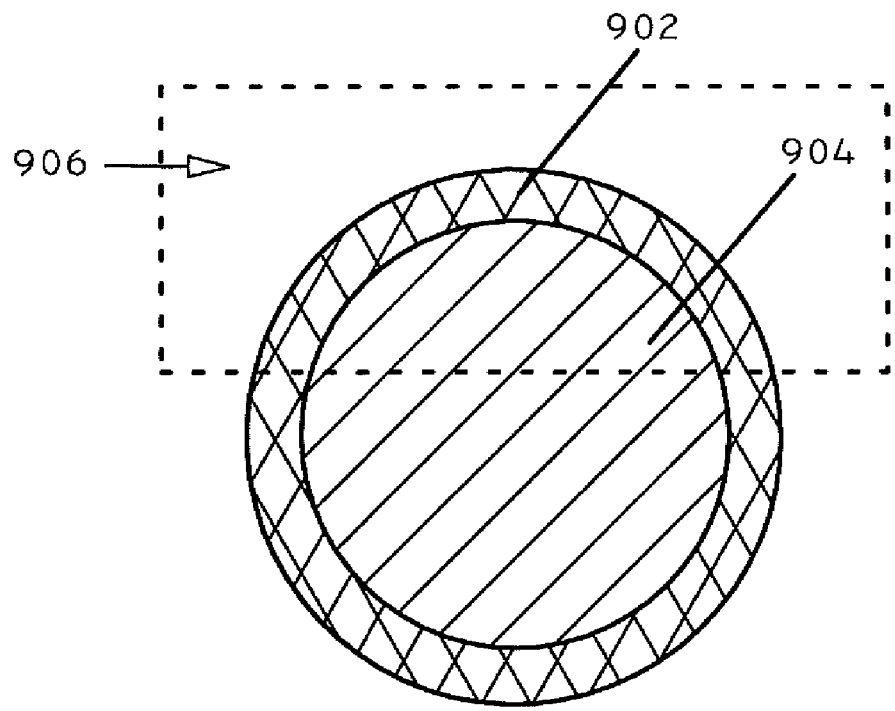
FIG. 10 is a schematic cross-sectional view of a coated substrate.
Figure 11:
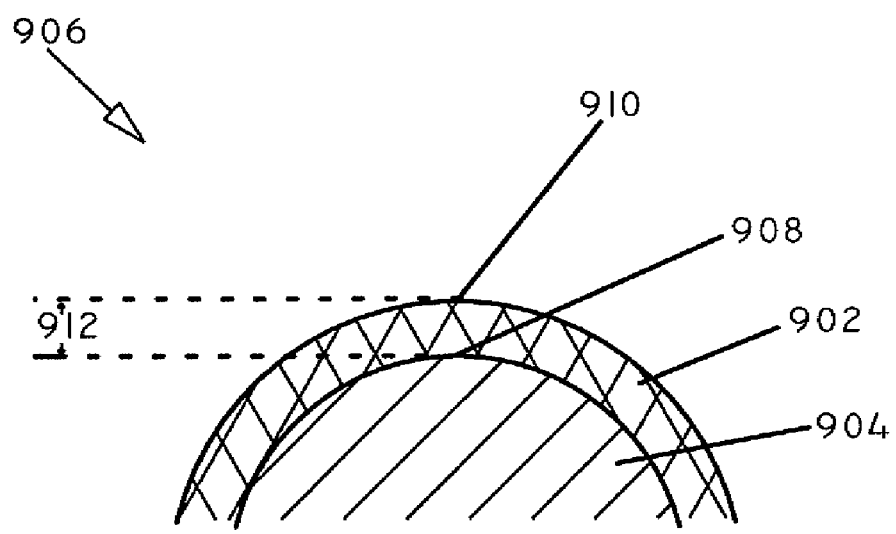
FIG. 11 is a schematic cross-sectional view of a portion of the coated substrate of FIG. 10.

Referring now to FIG. 10, an exemplary substrate 904 is shown with a coating 902 disposed thereon. FIG. 11 shows an enlarged view of a portion 906 of the substrate 904 and coating 902. The coating 902 has an inner surface 908 and an outer surface 910 with a distance 912 between the inner surface 908 and outer surface 910. The distance 912 can also be referred to as the depth of the coating 902. In some embodiments, the coating 902 may include two or more different components (polymers, active agents, etc.). The concentration of two or more components can vary with respect to each other over the depth of the coating 902. Thus, the relative concentration of a component can form a concentration gradient through the depth of the coating.

By way of example, in an embodiment, a first polymer composition including a first polymer can be supplied from a first composition delivery conduit at a constant rate while a second polymer composition including a second polymer can be supplied from a second composition delivery conduit at a rate that is varied (increased or decreased) as the coating is applied to the substrate. The delivery rate of the second polymer composition can be varied in either a continuous or stepped manner, to create a continuous or stepped concentration gradient respectively. As an example, the apparatus shown in FIG. 1, and described above, can be used to apply two polymer compositions in this manner. The result is a coating layer that has different concentrations of the first polymer relative to the second polymer at the inner surface 908 in comparison to at the outer surface 910.

As an illustration of this configuration, referring to Table 1 below, the concentrations of polymer A and polymer B are shown in wt. % as a function of the depth within the coating layer. As can be seen in Table 1, there is a concentration gradient of Polymer A going from 50 wt. % to 0 wt. % in between the inner surface and the outer surface. Similarly, there is a concentration gradient of Polymer B going from 50 wt. % to 100 wt. % in between the inner surface and the outer surface.

TABLE 1

|  | Depth | Polymer A (wt. %) | Polymer B (wt. %) |
| --- | --- | --- | --- |
| Inner Surface | 20 μm | 50 | 50 |
|  | 18 μm | 45 | 55 |
|  | 16 μm | 40 | 60 |
|  | 14 μm | 35 | 65 |
|  | 12 μm | 30 | 70 |
|  | 10 μm | 25 | 75 |
|  | 8 μm | 20 | 80 |
|  | 6 μm | 15 | 85 |
|  | 4 μm | 10 | 90 |
|  | 2 μm | 5 | 95 |
| Outer Surface | 0 μm | 0 | 100 |

It will be appreciated that the rate of application of any of the coating components (polymers, active agents, etc.) can be varied as the coating is deposited onto the surface of the substrate. Accordingly, any type of desired concentration gradient can be achieved. Table 2 below shows the concentrations of polymer A and polymer B in wt. % as a function of the depth within the coating layer in another example. However, in this example, the concentration gradient of Polymer A goes from 100 wt. % to 50 wt. % in between the inner surface and the outer surface and the concentration gradient of Polymer B goes from 0 wt. % to 50 wt. % in between the inner surface and the outer surface.

TABLE 2

|  | Depth | Polymer A (wt. %) | Polymer B (wt. %) |
| --- | --- | --- | --- |
| Inner Surface | 20 μm | 100 | 0 |
|  | 18 μm | 95 | 5 |
|  | 16 μm | 90 | 10 |
|  | 14 μm | 85 | 15 |
|  | 12 μm | 80 | 20 |
|  | 10 μm | 75 | 25 |
|  | 8 μm | 70 | 30 |
|  | 6 μm | 65 | 35 |
|  | 4 μm | 60 | 40 |
|  | 2 μm | 55 | 45 |
| Outer Surface | 0 μm | 50 | 50 |

Creating a coating layer having concentration gradients of the components can be desirable. By way of example, where polymer A has adhesive properties (such as with polyethylene-co-vinyl acetate), it can be desirable to increase Polymer A's relative concentration at the inner surface where the coating contacts the substrate surface, such as in the example configuration described in Table 2.

It will also be appreciated that coatings having a concentration gradient of active agent relative to one or more polymers can also be created in accordance with embodiments of the invention. By way of example, in an embodiment, a first polymer composition can be supplied from a first composition delivery conduit at a given rate, a second polymer composition can be supplied from a second composition delivery conduit at a given rate, and an active agent composition can be supplied from a third composition delivery conduit at a rate that is varied (increased or decreased) as the coating is applied to the substrate. The rate of active agent composition delivery can be varied in either a continuous or stepped manner, to create a continuous or stepped concentration gradient respectively. As an example, the apparatus shown in FIG. 6, and described above, can be used to apply the active agent and polymeric components in this manner. The result is a coating layer that has different concentrations of the active agent relative to the polymeric components at the inner surface 908 in comparison to at the outer surface 910. As a specific example, Table 3 below shows the concentrations of an active agent, polymer A, and polymer B in wt. % as a function of the depth within the coating layer.

TABLE 3

|  | Depth | Active Agent (wt. %) | Polymer A (wt. %) | Polymer B (wt. %) |
|---|---|---|---|---|
| Inner Surface | 22 μm | 0 | 50 | 50 |
|  | 20 μm | 4 | 48 | 48 |
|  | 18 μm | 8 | 46 | 46 |
|  | 16 μm | 12 | 44 | 44 |
|  | 14 μm | 16 | 42 | 42 |
|  | 12 μm | 20 | 40 | 40 |
|  | 10 μm | 24 | 38 | 38 |
|  | 8 μm | 28 | 36 | 36 |
|  | 6 μm | 32 | 34 | 34 |
|  | 4 μm | 36 | 32 | 32 |
|  | 2 μm | 40 | 30 | 30 |
| Outer Surface | 0 μm | 44 | 28 | 28 |

While examples of coatings with concentration gradients described above had two 5 polymers (A and B), it will be appreciated that coatings can be formed with concentration gradients of one, two, three, or more different polymers. By way of example, referring to Table 4 below, an example of a gradient coating with three different polymers (A, B, and C) and an active agent is shown.

TABLE 4

|  | Depth | Active Agent (wt. %) | Polymer A (wt. %) | Polymer B (wt. %) | Polymer C (wt. %) |
|---|---|---|---|---|---|
| Inner Surface | 22 μm | 10 | 30 | 30 | 30 |
|  | 20 μm | 10 | 32 | 29 | 29 |
|  | 18 μm | 10 | 34 | 28 | 28 |
|  | 16 μm | 10 | 36 | 27 | 27 |
|  | 14 μm | 10 | 38 | 26 | 26 |
|  | 12 μm | 10 | 40 | 25 | 25 |
|  | 10 μm | 10 | 42 | 24 | 24 |
|  | 8 μm | 10 | 44 | 23 | 23 |
|  | 6 μm | 10 | 46 | 22 | 22 |
|  | 4 μm | 10 | 48 | 21 | 21 |
|  | 2 μm | 10 | 50 | 20 | 20 |
| Outer Surface | 0 μm | 10 | 52 | 19 | 19 |

In addition, coatings with concentration gradients of multiple different types of components can be formed. It will also be understood that coating layers having concentration gradients can be disposed on a substrate with or without other coating layers on top of them or underneath them.

Further Embodiments of the Invention

In an embodiment, the invention includes an apparatus for applying a coating to a medical device including a spray nozzle and a plurality of coating composition supply conduits configured to separately deliver coating compositions to the surface of the spray nozzle. In an embodiment, the plurality of coating composition supply conduits include a first coating composition supply conduit configured to deliver a first coating composition onto the exterior surface of the spray nozzle and a second coating composition supply conduit configured to deliver a second coating composition onto the exterior surface of the spray nozzle. In an embodiment, the apparatus includes a first coating composition pump in fluid communication with the first coating composition supply conduit. In an embodiment, the invention includes a first coating composition supply reservoir in fluid communication with the first coating composition pump. In an embodiment, the invention includes a first coating composition supply reservoir including an amount of the first coating composition, the first coating composition including a solvent immiscible with a component of the second coating composition. In an embodiment, the apparatus includes a second coating composition pump in fluid communication with the second coating composition supply conduit. In an embodiment, the apparatus includes a second coating composition supply reservoir in fluid communication with the second coating composition pump. In an embodiment, the apparatus includes a second coating composition supply reservoir including an amount of the second coating composition, the second coating composition including a solvent immiscible with a component of the first coating composition. In an embodiment, at least one of the first and second coating compositions comprises a polymer. The polymer can include a first polymer component including at least one poly(alkyl)(meth)acrylate and a second polymer component including poly(ethylene-co-vinyl acetate), wherein the second polymer component is selected from the group consisting of poly(ethylene-co-vinyl acetate) polymers having vinyl acetate concentrations of between about 10% and about 50% by weight. In an embodiment, the active agent causes a desired biological effect when administered in vivo to an animal. The spray nozzle can include an ultrasonic atomization surface. The spray nozzle can have an external atomization surface and the plurality of coating composition supply conduits can be configured to separately deliver coating compositions to the external atomization surface. In an embodiment, the coating composition supply conduits are separated from the external atomization surface by an air gap. The air gap can be from about 0.05 mm to about 1.0 mm. In an embodiment, the air gap can be from about 0.2 mm to about 0.5 mm. However, in some embodiments, the coating composition supply conduits can contact the atomization surface. The apparatus can include a spray arm coupled to the nozzle. The apparatus can include a device rotator coupled to the medical device.

In an embodiment, the invention includes a method of applying a coating to a medical device including applying a first composition onto the surface of a spray nozzle; applying a second composition onto the surface of the spray nozzle; generating a spray stream with the nozzle; and directing the spray stream at the medical device. Applying a first composition onto the surface of a spray nozzle and applying a second composition onto the surface of a spray nozzle can be performed simultaneously. The first composition can include an active agent and a first solvent and the second composition can include a polymer and a second solvent. The polymer can include a first polymer component including at least one poly(alkyl)(meth)acrylate and a second polymer component including poly(ethylene-co-vinyl acetate), wherein the second polymer component is selected from the group consisting of poly(ethylene-co-vinyl acetate) polymers having vinyl acetate concentrations of between about 10% and about 50% by weight. In an embodiment, the second solvent includes a compound that is immiscible with the first solvent. In an embodiment, the active agent causes a desired biological effect when administered in vivo to an animal. In an embodiment, the active agent includes a macromolecular active agent. In an embodiment, the macromolecular active agent is a polypeptide. The spray nozzle can have an ultrasonic atomization surface. In an embodiment, the spray nozzle has an external atomization surface and the plurality of coating composition supply conduits configured to separately deliver coating compositions to the external atomization surface.

In an embodiment, the invention includes a method of applying a coating to a medical device including applying a first composition from a first spray nozzle while simultaneously applying a second composition from a second spray nozzle, the first and second spray nozzles creating spray streams; and directing the spray streams at the medical device. The first composition can include an active agent and a first solvent and the second composition can include a polymer and a second solvent. In an embodiment, the second solvent includes a compound that is immiscible with the first solvent.

In an embodiment, the invention includes a coating layer configured to control elution of an active agent, including a first polymer; and a second polymer; the coating layer defining an inner surface and an outer surface; wherein the concentration of the first polymer relative to the second polymer forms a gradient between the inner surface and the outer surface. In an embodiment, the gradient is substantially continuous between the inner surface and the outer surface. In an embodiment, the gradient is continuous between the inner surface and the outer surface. In an embodiment, the gradient is stepped between the inner surface and the outer surface. In an embodiment, the concentration of the second polymer relative to the first polymer is greater at the inner surface than at the outer surface. In an embodiment, the distance between the inner surface and the outer surface is from about 1 μm to about 100 μm. In an embodiment, the coating layer further includes an active agent. In an embodiment, the first polymer includes poly(n-butyl methacrylate) and the second polymer comprises poly(ethylene-co-vinyl acetate). In an embodiment, the first polymer comprises poly(n-butyl methacrylate) and the second polymer comprises polybutadiene.

In an embodiment, the invention includes an active agent eluting coating including a first polymer, a second polymer, and an active agent, the coating defining an inner surface and an outer surface, wherein the concentration of the first polymer relative to the second polymer decreases between the inner surface and the outer surface. In an embodiment, the concentration of the first polymer relative to the second polymer decreases continuously between the inner surface and the outer surface. In an embodiment, the concentration of the first polymer relative to the second polymer decreases in a stepped manner between the inner surface and the outer surface. In an embodiment, the distance between the inner surface and the outer surface is from about 1 μm to about 100 μm. In an embodiment, the first polymer comprises poly(n-butyl methacrylate) and the second polymer comprises poly(ethylene-co-vinyl acetate). In an embodiment, the first polymer comprises poly(n-butyl methacrylate) and the second polymer comprises polybutadiene.

In an embodiment, the invention includes a coating layer including a first polymer, a second polymer, and an active agent, the coating defining an inner surface and an outer surface, wherein the concentration of the first polymer relative to the second polymer forms a gradient between the inner surface and the outer surface. In an embodiment, the gradient is continuous between the inner surface and the outer surface. In an embodiment, the gradient is stepped between the inner surface and the outer surface. In an embodiment, the concentration of the first polymer relative to the second polymer is greater at the outer surface than at the inner surface.

It will be understood that changes and modifications may be made without departing from the scope and the spirit of the invention as hereinafter claimed. The invention will now be demonstrated referring to the following non-limiting examples.

EXAMPLES

Example 1

Application of a Coating Containing BSA Using a Dual Supply Feed Ultrasonic Spray System Poly-n-butylmethacrylate (PBMA) and polyethylene-co-vinyl acetate (PEVA) were combined with a solvent mixture composed of 80% by volume chloroform and 20% by volume methanol to form a polymer composition having 5 mg/ml PBMA and 5 mg/ml PEVA (total solids concentration of 10 mg/ml). Bovine serum albumin (BSA) was mixed with phosphate buffered saline (PBS) to form an active agent composition having a concentration of 30 mg/ml BSA.

Three stainless steel stents were obtained from Laserage Technology Corporation, Waukegan, Ill. Each stent was weighed prior to coating application. Pre-coating weight is shown below in Table 5.

The polymer composition was applied onto the exterior surface of an ultrasonic nozzle (60 KHz ultrasonic nozzle from Sono-Tek, Milton, N.Y.) operating at about 0.5 to 1.5 watts. The polymer composition was applied through a first supply tube at a rate of 0.06 ml/minute. Simultaneously, the active agent composition was applied onto the ultrasonic nozzle through a second supply tube at a rate of 0.02 ml/minute. Thus, the polymer composition was supplied at a rate three times as fast as the active agent composition (0.06 ml/minute versus 0.02 ml/minute). However, since the polymer composition had a total solids concentration that was one third of the active agent composition (10 mg/ml versus 30 mg/ml), the total weight of polymers (PBMA and PEVA) supplied per minute was equal to the total weight of BSA supplied per minute (0.6 mg/minute for both).

The ultrasonic nozzle generated an atomized stream of coating material that was directed at the stents. The ultrasonic nozzle was passed back and forth over the stents in a direction parallel to their main axis as the stents were rotated by a device rotator. After coating, the stents were dried in a vacuum oven at ambient temperature for 24 hours. The stents were weighed again, the total coating weight was calculated as shown in Table 5 below. Because the polymers and the BSA were applied with the same total solids per minute rate (0.6 mg/minute), the amount of BSA present in the coatings was calculated as half of the total coating weight as measured after drying (see Table 5).

TABLE 5

| Stent # | Pre-Coating Weight (mg) | Post-Coating Weight (mg) | Coating Weight (mg) | BSA in Coating (mg) |
|---|---|---|---|---|
| 1 | 33.863 | 34.405 | 0.542 | 0.271 |
| 2 | 30.587 | 31.095 | 0.511 | 0.256 |
| 3 | 33.586 | 34.073 | 0.487 | 0.244 |

The surface of the coating applied to Stent #1 was then examined using SEM (scanning electron microscopy), AFM (atomic force microscopy), and IR (infrared) techniques. The data revealed that the surface of the coating applied to stent #1 was substantially continuous over the surface of the stent substrate.

The elution of the BSA from stents 2 and 3 was then tested. Each of the stents was placed in a container with PBS and stored at 37° C. After 45.5 hours, the PBS solution was withdrawn from each container and the concentration of BSA that eluted into each solution was calculated using BCA-UV analysis. After withdrawal of the PBS solution, fresh PBS solution was put into each container. This measurement procedure was repeated at various time intervals as shown in Table 6 below.

TABLE 6

| Time Point | Cumulative Amount of BSA Eluted (Cumulative % of BSA Eluted) | |
|---|---|---|
| | Stent # 2 | Stent # 3 |
| 45.5 hrs | 33.41 µg (13.08%) | 28.36 µg (11.65%) |
| 94.5 hrs | 45.83 µg (17.94%) | 38.42 µg (15.78%) |
| 142.5 hrs | 58.85 µg (23.03%) | 66.31 µg (27.23%) |
| 166.5 hrs | 60.42 µg (23.65%) | 66.91 µg (27.48%) |
| 190.5 hrs | 61.19 µg (23.95%) | 67.34 µg (27.66%) |
| 215 hrs | 61.93 µg (24.24%) | 67.75 µg (27.82%) |
| 239 hrs | 62.23 µg (24.36%) | 68.11 µg (27.97%) |
| 333 hrs | 63.04 µg (24.67%) | 68.76 µg (28.24%) |

Figure 12:
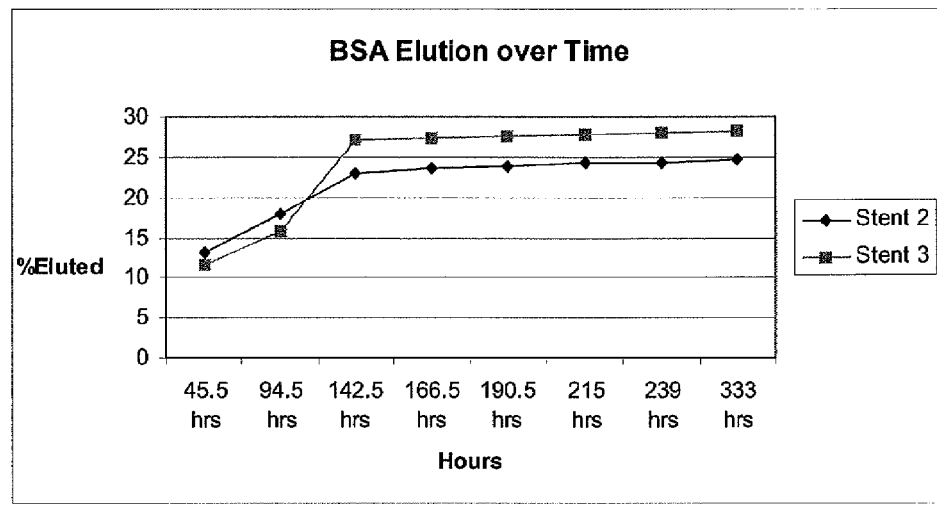
FIG. 12 is a graph of selected data generated in Example 1.

As shown in FIG. 12, the data in this example show that the coating applied to the stents provided controlled release of BSA over an extended period of time. BSA serves as a model for macromolecular agents because it is a protein and has a molecular weight of approximately 67 kD. Thus, the data show that methods of the invention can be used to create coatings providing desired release properties of active agents. In particular, the data show that methods of the invention can be used to create coatings including amounts of incompatible solvents, such as chloroform and PBS.

Example 2

Application of a Coating Containing BSA Using a Dual Supply Tube Ultrasonic Spray System While Altering Protein Loading 33 wt. % BSA Loading:
Poly-n-butylmethacrylate (PBMA) and polyethylene-co-vinyl acetate (PEVA) were combined with chloroform to form a polymer composition having 10 mg/ml PBMA and 10 mg/ml PEVA (total solids concentration of 20 mg/ml). Bovine serum albumin (BSA) was mixed with phosphate buffered saline (PBS) to form an active agent composition having a concentration of 30 mg/ml BSA.

Three stainless steel stents were obtained from Laserage Technology Corporation, Waukegan, Ill. Each stent was weighed prior to coating application. Pre-coating weight is shown below in Table 7.

The polymer composition was applied onto the exterior surface of an ultrasonic nozzle (60 KHz ultrasonic nozzle from Sono-Tek, Milton, N.Y.) operating at about 0.5 to 1.5 watts. The polymer composition was delivered through a first supply tube at a rate of 0.06 ml/minute. Simultaneously, the active agent composition was applied onto the ultrasonic nozzle through a second supply tube at a rate of 0.02 ml/minute. Thus, the total weight of polymers (PBMA and PEVA) supplied per minute was twice as large as the total weight of BSA supplied per minute.

62.5 wt. % BSA Loading:
Poly-n-butylmethacrylate (PBMA) and polyethylene-co-vinyl acetate (PEVA) were combined with chloroform to form a polymer composition having 5 mg/ml PBMA and 5 mg/ml PEVA (total solids concentration of 10 mg/ml). Bovine serum albumin (BSA) was mixed with phosphate buffered saline (PBS) to form an active agent composition having a concentration of 50 mg/ml BSA.

Three stainless steel stents were obtained from Laserage Technology Corporation, Waukegan, Ill. Each stent was weighed prior to coating application. Pre-coating weight is shown below in Table 7. The polymer composition was applied onto the ultrasonic nozzle (as above) through a first supply tube at a rate of 0.06 ml/minute. Simultaneously, the active agent composition was applied onto the ultrasonic nozzle through a second supply tube at a rate of 0.02 ml/minute.

The ultrasonic nozzle generated an atomized stream of coating material that was directed at the stents. The ultrasonic nozzle was passed back and forth over the stents in a direction parallel to their main axis as the stents were rotated by a device rotator. After coating, the stents were dried in a vacuum oven at ambient temperature for 24 hours. The stents were weighed again, the total coating weight was calculated as shown in Table 7 below.

TABLE 7

| Stent # | Pre-Coating Weight (mg) | Post-Coating Weight (mg) | Coating Weight (mg) | BSA in Coating (µg) |
|---|---|---|---|---|
| 70 (33 wt. % BSA) | 29.963 | 30.595 | .632 | 208.56 |
| 71 (33 wt. % BSA) | 30.469 | 31.117 | .648 | 213.84 |
| 72 (33 wt. % BSA) | 32.298 | 32.934 | .636 | 209.88 |
| 76 (62.5 wt. % BSA) | 31.772 | 32.375 | .603 | 379.89 |
| 77 (62.5 wt. % BSA) | 31.174 | 31.768 | .594 | 374.22 |
| 78 (62.5 wt. % BSA) | 34.529 | 35.101 | .572 | 360.36 |

The stents were then tested for elution of BSA. Each of the stents were placed in separate containers with PBS and stored at 37° C. At various time points, the PBS solution was withdrawn from each container and the concentration of BSA that eluted into each solution was calculated using BCA-UV analysis. After withdrawal of the PBS solution, fresh PBS solution was put into each container. The results are shown in Table 8 below (Table 9 shows the same data as Table 8 converted into percentage format).

TABLE 8

| | Total Amount of BSA Eluted (µg) | | | | |
|---|---|---|---|---|---|
| Stent | 24 hrs | 48 hrs | 72.5 hrs | 96.5 hrs | 190.5 hrs |
| 70 | 88.312 | 104.686 | 108.185 | 109.101 | 109.561 |
| 71 | 97.423 | 118.458 | 120.906 | 121.112 | 121.519 |
| 72 | 86.981 | 112.456 | 114.934 | 115.109 | 115.355 |
| 76 | 145.185 | 201.739 | 210.204 | 212.602 | 213.062 |
| 77 | 200.097 | 229.378 | 231.975 | 232.335 | 232.608 |
| 78 | 196.775 | 228.829 | 231.515 | 231.690 | 231.829 |

TABLE 9

| | Total Amount of BSA Eluted (%) | | | | |
|---|---|---|---|---|---|
| Stent | 24 hrs | 48 hrs | 72.5 hrs | 96.5 hrs | 190.5 hrs |
| 70 | 42.34% | 50.19% | 51.87% | 52.31% | 52.53% |
| 71 | 45.56% | 55.40% | 56.54% | 56.64% | 56.83% |
| 72 | 41.44% | 53.58% | 54.76% | 54.85% | 54.96% |
| 76 | 38.22% | 53.10% | 55.33% | 55.96% | 56.09% |
| 77 | 53.47% | 61.29% | 61.99% | 62.09% | 62.16% |
| 78 | 54.61% | 63.50% | 64.25% | 64.29% | 64.33% |

Figure 13:
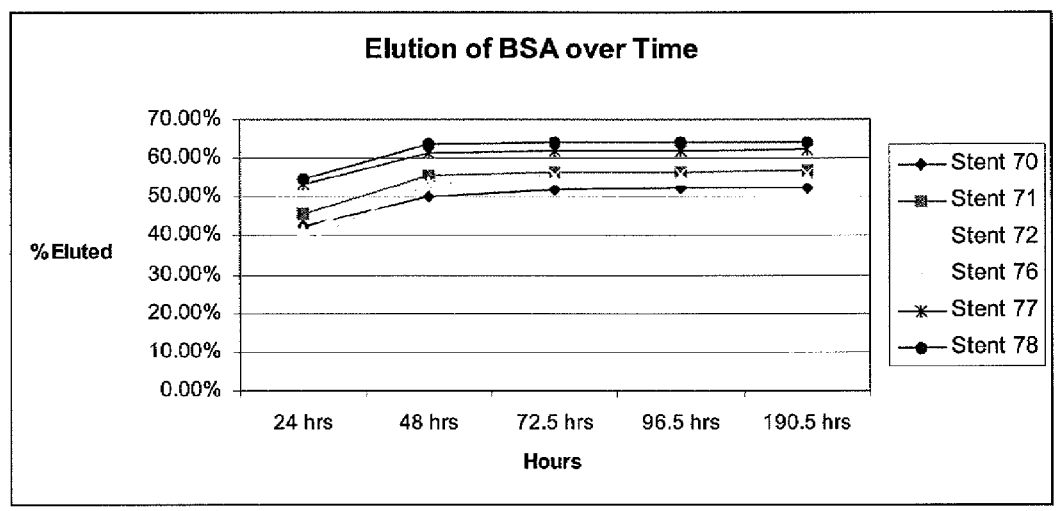
FIG. 13 is a graph of selected data generated in Example 2.

As illustrated in FIG. 13, a lesser amount of BSA eluted from the coatings having a 33% BSA load than from the coatings having a 62.5% BSA load. Therefore, the data in this example show that elution rate can be changed by changing the amount of the active agent in the coating relative to the amount of the polymers. The data also show that a coater having multiple composition supply tubes can be used to vary the loading of an active agent relative to the polymers because the concentrations of the active agent composition or the polymer composition, or both, can be easily changed.

Example 3

Application of a Coating Containing Sulfasalazine Using a Dual Supply Tube Ultrasonic Spray System An active agent composition of 20 mg/ml sulfasalazine (Sigma) was prepared in an 80/20 (vol %) acetonitrile/$H_2O$ mixture. NaOH was added to the composition at a 0.05N concentration. The resulting composition was found to be clear and without suspended particles of the active agent.

A first polymer stock composition (PBMA/$CHCl_3$) of 20 mg/ml poly(n-butyl methacrylate) (PBMA) was prepared in a solvent of 100% chloroform.

A second polymer stock composition (PEVA/$CHCl_3$) of 20 mg/ml poly(ethylene-co-vinyl acetate) (PEVA) was prepared in a solvent of 100% chloroform.

A third polymer stock composition (PBMA/THF) of 20 mg/ml poly(n-butyl methacrylate) (PBMA) was prepared in a solvent of 100% tetrahydrofuran.

A fourth polymer stock composition (PEVA/THF) of 20 mg/ml poly(ethylene-co-vinyl acetate) (PEVA) was prepared in a solvent of 100% tetrahydrofuran.

A first set of MP-35N alloy coils (N=6) (Lake Region Manufacturing, Inc., Chaska, Minn.) were coated with a base coat according to the following procedure. The active agent composition was delivered through a first supply conduit onto a first ultrasonic spray nozzle (60 KHz ultrasonic nozzle from Sono-Tek, Milton, N.Y.) at a rate of 0.02 ml/min. Simultaneously, a 50/50 mix of the first polymer stock composition (PBMA/$CHCl_3$) and the second polymer stock composition (PEVA/$CHCl_3$) were applied through a second supply conduit onto a second ultrasonic spray nozzle (60 KHz ultrasonic nozzle from Sono-Tek, Milton, N.Y.) at a rate of 0.04 ml/min.

The first and second spray nozzles were positioned with the tips approximately 1 cm apart from each other. The first and second spray nozzles were mounted on the same spraying arm so that any movements of the arm did not affect the positioning of the nozzles with respect to one another. Both the first and second spray nozzles were operated at about 0.5 to 1.5 watts. The relative humidity in the air surrounding the spray nozzles was approximately 25% to 30% relative humidity. Coils were held in place under the spray nozzle with a pin vise configured to rotate the coils about their longitudinal axis. The vertical distance between the coils and the spray nozzles was approximately one centimeter.

A stream of nitrogen gas (3.5 PSI) was used with each spray nozzle in order to focus and direct the spray generated by each spray nozzle. The first and second ultrasonic nozzles each generated spray streams that were aimed to intersect at a point above the coil. The spraying arm moved the spray nozzles back and forth over the length of the coil while the pin vise rotated the coil. For three of the six coils, only a base coat was deposited. For the remaining three coils in this set, a top coat was applied after application of the base coat. Specifically, the first polymer stock composition (PBMA/$CHCl_3$) having 20 mg/ml poly(n-butyl methacrylate) (PBMA) was applied through the second supply conduit onto the second ultrasonic spray nozzle at a rate of 0.06 ml/min. The coating weights are shown below in Table 10. After drying overnight, the coils were evaluated using optical microscopy and the coatings were uniformly smooth and clear.

A second set of MP-35N alloy coils (N=6) (Lake Region Manufacturing, Inc., Chaska, Minn.) were coated with a base coat according to the following procedure. The active agent composition was delivered through a first supply conduit onto a first ultrasonic spray nozzle (60 KHz ultrasonic nozzle from Sono-Tek, Milton, N.Y.) at a rate of 0.04 ml/min. Simultaneously, a 50/50 mix of the first polymer stock composition (PBMA/$CHCl_3$) and the second polymer stock composition (PEVA/$CHCl_3$) were applied through a second supply conduit onto a second ultrasonic spray nozzle (60 KHz ultrasonic nozzle from Sono-Tek, Milton, N.Y.) at a rate of 0.04 ml/min. The first and second spray nozzles were positioned with the tips approximately 1 cm apart from each other. The first and second spray nozzles were same spraying arm so that any movements of the arm did not affect the positioning of the nozzles with respect to one another. Both the first and second spray nozzles were operated at about 0.5 to 1.5 watts. The relative humidity in the air surrounding the spray nozzles was approximately 25% to 30% relative humidity. Coils were held in place under the spray nozzle with a pin vise configured to rotate the coils about their longitudinal axis. The vertical distance between the coils and the spray nozzles was approximately one centimeter. A stream of nitrogen gas (3.5 PSI) was used with each spray nozzle in order to focus and direct the spray generated by each spray nozzle. The first and second ultrasonic nozzles each generated spray streams that were aimed to intersect at a point above the coil. The spraying arm moved the spray nozzles back and forth over the length of the coil while the pin vise rotated the coil. For three of the six coils, only a base coat was deposited. For the remaining three coils in this set, a top coat was applied after application of the base coat. Specifically, the first polymer stock composition (PBMA/$CHCl_3$) having 20 mg/ml poly(n-butyl methacrylate) (PBMA) was applied through the second supply conduit onto the second ultrasonic spray nozzle at a rate of 0.06 ml/min. The coating weights are shown below in Table 10. After drying overnight, the coils were evaluated using optical microscopy and the coatings were uniformly smooth and clear.

A third set of MP-35N alloy coils (N=3) (Lake Region Manufacturing, Inc., Chaska, Minn.) were coated with a base coat according to the following procedure. The active agent composition was delivered through a first supply conduit onto a first ultrasonic spray nozzle (60 KHz ultrasonic nozzle from Sono-Tek, Milton, N.Y.) at a rate of 0.04 ml/min. Simultaneously, a 50/50 mix of the third polymer stock composition (PBMA/THF) and the fourth polymer stock composition (PEVA/THF) were applied through a second supply conduit onto a second ultrasonic spray nozzle (60 KHz ultrasonic nozzle from Sono-Tek, Milton, N.Y.) at a rate of 0.04 ml/min. The first and second spray nozzles were positioned with the tips approximately 1 cm apart from each other. The first and second spray nozzles were same spraying arm so that any movements of the arm did not affect the positioning of the nozzles with respect to one another. Both the first and second spray nozzles were operated at about 0.5 to 1.5 watts. The relative humidity in the air surrounding the spray nozzles was approximately 25% to 30% relative humidity. Coils were held in place under the spray nozzle with a pin vise configured to rotate the coils about their longitudinal axis. The vertical distance between the coils and the spray nozzles was approximately one centimeter. A stream of nitrogen gas (3.5 PSI) was used with each spray nozzle in order to focus and direct the spray generated by each spray nozzle. The first and second ultrasonic nozzles each generated spray streams that were aimed to intersect at a point above the coil. The spraying arm moved the spray nozzles back and forth over the length of the coil while the pin vise rotated the coil. The coating weights are shown below in Table 10. After drying overnight, the coils were evaluated using optical microscopy and the coatings were uniformly smooth and clear.

A fourth set of MP-35N alloy coils (N=3) (Lake Region Manufacturing, Inc., Chaska, Minn.) were coated with a base coat according to the following procedure. The active agent composition was delivered through a first supply conduit onto a first ultrasonic spray nozzle (60 KHz ultrasonic nozzle from Sono-Tek, Milton, N.Y.) at a rate of 0.025 ml/min. Simultaneously, a 50/50 mix of the third polymer stock composition (PBMA/THF) and the fourth polymer stock composition (PEVA/THF) were applied through a second supply conduit onto a second ultrasonic spray nozzle (60 KHz ultrasonic nozzle from Sono-Tek, Milton, N.Y.) at a rate of 0.05 ml/min. The first and second spray nozzles were positioned with the tips approximately 1 cm apart from each other. The first and second spray nozzles were same spraying arm so that any movements of the arm did not affect the positioning of the nozzles with respect to one another. Both the first and second spray nozzles were operated at about 0.5 to 1.5 watts. The relative humidity in the air surrounding the spray nozzles was approximately 25% to 30% relative humidity. Coils were held in place under the spray nozzle with a pin vise configured to rotate the coils about their longitudinal axis. The vertical distance between the coils and the spray nozzles was approximately one centimeter. A stream of nitrogen gas (3.5 PSI) was used with each spray nozzle in order to focus and direct the spray generated by each spray nozzle. The first and second ultrasonic nozzles each generated spray streams that were aimed to intersect at a point above the coil. The spraying arm moved the spray nozzles back and forth over the length of the coil while the pin vise rotated the coil. The coating weights are shown below in Table 10. After drying overnight, the coils were evaluated using optical microscopy and the coatings were uniformly smooth and clear.

A fifth set of MP-35N alloy coils (N=3) (Lake Region Manufacturing, Inc., Chaska, Minn.) were coated with a base coat according to the following procedure. The active agent composition was delivered through a first supply conduit onto a first ultrasonic spray nozzle (60 KHz ultrasonic nozzle from Sono-Tek, Milton, N.Y.) at a rate of 0.025 ml/min. Simultaneously, a 33/67 mix of the third polymer stock composition (PBMA/THF) and the fourth polymer stock composition (PEVA/THF) were applied through a second supply conduit onto a second ultrasonic spray nozzle (60 KHz ultrasonic nozzle from Sono-Tek, Milton, N.Y.) at a rate of 0.05 ml/min. The first and second spray nozzles were positioned with the tips approximately 1 cm apart from each other. The first and second spray nozzles were same spraying arm so that any movements of the arm did not affect the positioning of the nozzles with respect to one another. Both the first and second spray nozzles were operated at about 0.5 to 1.5 watts. The relative humidity in the air surrounding the spray nozzles was approximately 25% to 30% relative humidity. Coils were held in place under the spray nozzle with a pin vise configured to rotate the coils about their longitudinal axis. The vertical distance between the coils and the spray nozzles was approximately one centimeter. A stream of nitrogen gas (3.5 PSI) was used with each spray nozzle in order to focus and direct the spray generated by each spray nozzle. The first and second ultrasonic nozzles each generated spray streams that were aimed to intersect at a point above the coil. The spraying arm moved the spray nozzles back and forth over the length of the coil while the pin vise rotated the coil. The coating weights are shown below in Table 10. After drying overnight, the coils were evaluated using optical microscopy and the coatings were uniformly smooth and clear.

A sixth set of MP-35N alloy coils (N=3) (Lake Region Manufacturing, Inc., Chaska, Minn.) were coated with a base coat according to the following procedure. The active agent composition was delivered through a first supply conduit onto a first ultrasonic spray nozzle (60 KHz ultrasonic nozzle from Sono-Tek, Milton, N.Y.) at a rate of 0.025 ml/min. Simultaneously, a 67/33 mix of the third polymer stock composition (PBMA/THF) and the fourth polymer stock composition (PEVA/THF) respectively were applied through a second supply conduit onto a second ultrasonic spray nozzle (60 KHz ultrasonic nozzle form Sono-Tek, Milton, N.Y.) at a rate of 0.05 ml/min. The first and second spray nozzles were positioned with the tips approximately 1 cm apart from each other. The first and second spray nozzles were same spraying arm so that any movements of the arm did not affect the positioning of the nozzles with respect to one another. Both the first and second spray nozzles were operated at about 0.5 to 1.5 watts. The relative humidity in the air surrounding the spray nozzles was approximately 25% to 30% relative humidity. Coils were held in place under the spray nozzle with a pin vise configured to rotate the coils about their longitudinal axis. The vertical distance between the coils and the spray nozzles was approximately one centimeter. A stream of nitrogen gas (3.5 PSI) was used with each spray nozzle in order to focus and direct the spray generated by each spray nozzle. The first and second ultrasonic nozzles each generated spray streams that were aimed to intersect a point above the coil. The spraying arm moved the spray nozzles back and forth over the length of the coil while the pin vise rotated the coil. The coating weights are shown below in Table 10. After drying overnight, the coils were evaluated using optical microscopy and the coatings were uniformly smooth and clear.

TABLE 10

| Set | Coil # | Base Coating Wt. (µg) | Top Coating Wt. (µg) |
| --- | --- | --- | --- |
| 1 | 1 | 986 | NA |
| 1 | 2 | 1011 | NA |
| 1 | 3 | 1007 | NA |
| 1 | 4 | 931 | 279 |
| 1 | 5 | 923 | 281 |
| 1 | 6 | 935 | 280 |
| 2 | 7 | 914 | NA |
| 2 | 8 | 927 | NA |
| 2 | 9 | 925 | NA |
| 2 | 10 | 903 | 279 |
| 2 | 11 | 938 | 281 |
| 2 | 12 | 903 | 280 |
| 3 | 13 | 965 | NA |
| 3 | 14 | 974 | NA |
| 3 | 15 | 963 | NA |
| 4 | 16 | 933 | NA |
| 4 | 17 | 942 | NA |
| 4 | 18 | 945 | NA |
| 5 | 19 | 1362 | NA |
| 5 | 20 | 1355 | NA |
| 5 | 21 | 1375 | NA |
| 6 | 22 | 1323 | NA |
| 6 | 23 | 1323 | NA |
| 6 | 24 | 1354 | NA |

Figure 14:
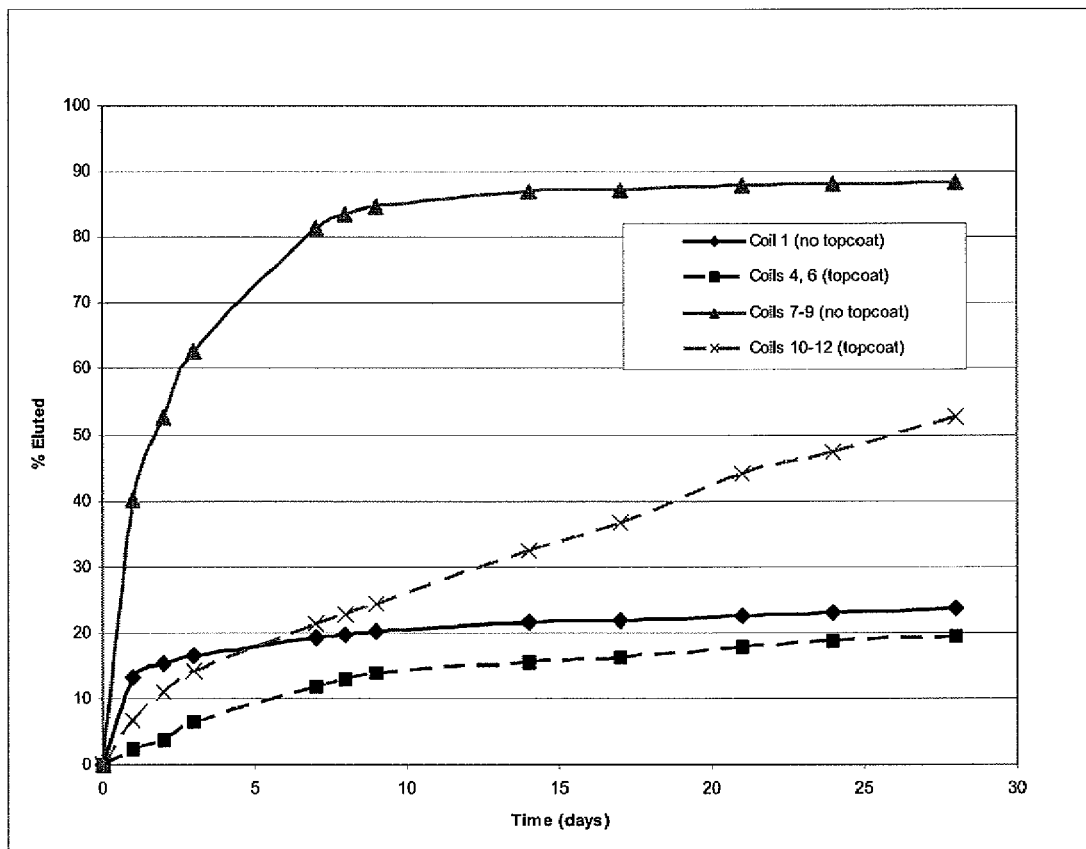
FIG. 14 is a graph of selected data generated in Example 3.

Elution of the coated coils was then evaluated. Elution was assessed using a SOTAX USP IV Flow-through Dissolution System (Sotax Corporation, Horsham, Pa.). The elution setup was closed-loop and therefore the same medium volume was maintained throughout the analysis. The elution medium was 0.01M phosphate buffered saline at a pH of 7.4 and a temperature of 37 degrees Celsius. Absorbance was measured using a UV spectrophotometer at the times shown in Table 11 below. The average elution data for each time point are shown below in Table 11 (elution from coils 2, 3 and 5 was not evaluated). Selected elution data is also shown in FIG. 14.

TABLE 11

| Time (days) | Coils (Cumulative % Eluted) | | | | | | | |
|---|---|---|---|---|---|---|---|---|
| | #1 | #4, #6 | #7–#9 | #10–#12 | #13–#15 | #16–#18 | #19–#21 | #22–#24 |
| 0 | 0.00 | 0.00 | 0.00 | 0.00 | 0.00 | 0.00 | 0.00 | 0.00 |
| 1 | 13.20 | 2.25 | 40.20 | 6.77 | 48.37 | 16.97 | 7.25 | 16.27 |
| 2 | 15.30 | 3.70 | 52.63 | 10.90 | 53.87 | 20.93 | 8.40 | 17.73 |
| 3 | 16.50 | 6.50 | 62.60 | 14.13 | 56.10 | 23.77 | 9.40 | 18.47 |
| 7 | 19.20 | 11.75 | 81.47 | 21.43 | 58.70 | 31.40 | 12.95 | 20.30 |
| 8 | 19.80 | 13.10 | 83.50 | 22.67 | 58.97 | 32.63 | 13.70 | 20.63 |
| 9 | 20.30 | 13.85 | 84.80 | 24.40 | 59.17 | 34.07 | 14.35 | 20.90 |
| 14 | 21.50 | 15.65 | 87.10 | 32.53 | 59.90 | 37.73 | 16.25 | 22.07 |
| 17 | 21.90 | 16.30 | 87.33 | 36.67 | 60.17 | 39.13 | 17.05 | 22.67 |
| 21 | 22.50 | 17.85 | 87.93 | 44.00 | 60.87 | 41.43 | 18.25 | 23.67 |
| 24 | 22.90 | 18.90 | 88.07 | 47.43 | 61.13 | 42.47 | 18.75 | 24.03 |
| 28 | 23.70 | 19.60 | 88.40 | 52.77 | 61.43 | 43.83 | 19.35 | 24.73 |

This example shows that a spraying system with dual spray nozzles can be effectively used to form coatings with multiple coating compositions including non-miscible solvents.

It should be noted that, as used in this specification and the appended claims, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, adapted, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific embodiments and techniques. However, it should be understood that many variations and modifications may be made while remaining within the spirit and scope of the invention.

The claims are:

1. An apparatus for applying a coating to a medical device comprising:
a first spray nozzle;
a first composition supply reservoir and a first coating composition disposed therein, the first coating composition comprising an active agent and a first solvent;
a first coating composition supply conduit configured to deliver the first coating composition to the first spray nozzle from the first composition supply reservoir;
a second spray nozzle;
a second composition supply reservoir and a second coating composition disposed therein, the second coating composition comprising a polymer and a second solvent, the second solvent immiscible with the first solvent;
a second coating composition supply conduit configured to deliver the second coating composition to the second spray nozzle from the second composition supply reservoir;
the first and second spray nozzles configured to produce first and second spray streams that intersect one another; and
a device holder configured to hold a medical device in the path of the first and second spray streams;
wherein the active agent is a therapeutic agent, and is insoluble in the second solvent and the polymer is insoluble in the first solvent.

2. The apparatus of claim 1, the first and second spray nozzles arranged so that the center of the first spray stream and the center of the second spray stream intersect one another at an intersection point disposed between the first and second spray nozzles and the medical device.

3. The apparatus of claim 2, the intersection point disposed above the device holder.

4. The apparatus of claim 1, the first spray nozzle comprising a first longitudinal axis and the second spray nozzle comprising a second longitudinal axis, the first and second spray nozzles arranged so that the first longitudinal axis intersects the second longitudinal axis at an angle comprising between about 5 and about 120 degrees.

5. The apparatus of claim 1, the first spray nozzle comprising a first spray tip, the second spray nozzle comprising a second spray tip, the first spray tip and the second spray tip disposed less than 5 cm apart.

6. The apparatus of claim 1, the first spray nozzle comprising a first spray tip, the second spray nozzle comprising a second spray tip, the first spray tip and the second spray tip disposed less than 2 cm apart.

7. The apparatus of claim 1, the first spray nozzle and the second spray nozzle comprising ultrasonic spray nozzles.

8. The apparatus of claim 1, further comprising:
a first pump connected to the first coating composition supply conduit; and a second pump connected to the second coating composition supply conduit.

9. The apparatus of claim 1, the device holder configured to rotate the medical device about an axis of rotation.

10. The apparatus of claim 1, further comprising a spray arm configured to move in a direction parallel to the axis of rotation of the device holder, the first and second spray nozzles disposed on the spray arm.

11. The apparatus of claim 1, the first coating composition supply conduit separated from the first spray nozzle by a first air gap and the second coating composition supply conduit separated from the second spray nozzle by a second air gap.

12. An apparatus for applying a coating to a medical device comprising:

an ultrasonic spray nozzle;

a first composition supply reservoir and a first coating composition disposed therein, the first coating composition comprising an active agent and a first solvent;

a first coating composition supply conduit configured to deliver the first coating composition onto the exterior surface of the ultrasonic spray nozzle;

a second composition supply reservoir and a second coating composition disposed therein, the second coating composition comprising a polymer and a second solvent, the second solvent immiscible with the first solvent; and a second coating composition supply conduit configured to deliver a second coating composition onto the exterior surface of the ultrasonic spray nozzle;

wherein the active agent is a therapeutic agent, and is insoluble in the second solvent and the polymer is insoluble in the first solvent.

13. The apparatus of claim 12, the first coating composition supply conduit disposed above the second coating composition supply conduit.

14. The apparatus of claim 12, further comprising a device rotator coupled to the medical device.

15. The apparatus of claim 1, the active agent comprising a polypeptide.

16. The apparatus of claim 12, the active agent comprising a polypeptide.

* * * * *